US008335992B2

(12) United States Patent
Skidmore et al.

(10) Patent No.: US 8,335,992 B2
(45) Date of Patent: Dec. 18, 2012

(54) VISUAL INDICATION OF SETTINGS CHANGES ON A VENTILATOR GRAPHICAL USER INTERFACE

(75) Inventors: John P. Skidmore, San Diego, CA (US); Olen D. Porter, Oceanside, CA (US); Marc E. Palmer, Trabuco Canyon, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 206 days.

(21) Appl. No.: 12/631,752

(22) Filed: Dec. 4, 2009

(65) Prior Publication Data

US 2011/0138309 A1    Jun. 9, 2011

(51) Int. Cl.
*G06F 3/048* (2006.01)
(52) U.S. Cl. .................. 715/771; 715/810; 715/764
(58) Field of Classification Search .................. 715/771, 715/810, 764
See application file for complete search history.

(56) References Cited

U.S. PATENT DOCUMENTS

| | | |
|---|---|---|
| 3,577,984 A | 5/1971 | Levy et al. |
| 3,659,590 A | 5/1972 | Jones et al. |
| 3,871,371 A | 3/1975 | Weigl |
| 3,940,742 A | 2/1976 | Hudspeth et al. |
| 3,961,624 A | 6/1976 | Weigl |
| 3,961,627 A | 6/1976 | Ernst et al. |
| 3,977,394 A | 8/1976 | Jones et al. |
| 3,991,304 A | 11/1976 | Hillsman |
| 3,996,928 A | 12/1976 | Marx |

(Continued)

FOREIGN PATENT DOCUMENTS

EP    0414777    3/1991

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Nicholas Augustine
*Assistant Examiner* — Erik Stitt
(74) *Attorney, Agent, or Firm* — Merchant & Gould P.C.

(57) ABSTRACT

This disclosure describes improved systems and methods for visualizing the application of changes to respiratory settings in a ventilatory system. Specifically, the present disclosure provides for a setup animation window that may be easily accessed from a setup icon, for example, and also provides for a settings animation window that may be easily accessed from any number of displayed ventilatory settings. In fact, the setup animation window may be directly accessed by touching, clicking, or otherwise selecting the setup icon and may expand from the setup icon to display any number of settings access elements. Alternatively, the settings animation window may be directly accessed by touching, clicking, or otherwise selecting any one of the displayed ventilatory settings and may expand from the displayed ventilatory settings to provide corresponding settings access elements. The corresponding settings access elements each corresponding to an individual ventilatory setting of the displayed ventilatory settings and useful for efficiently adjusting the displayed ventilatory settings. Ventilatory settings may be changed and accepted via either animation window. In one embodiment, upon accepting settings changes from the settings animation window, settings may appear to visually float or fade into the displayed ventilatory settings. In this embodiment, clinicians may view the settings changes as they are accepted and applied to the GUI.

13 Claims, 9 Drawing Sheets
(9 of 9 Drawing Sheet(s) Filed in Color)

U.S. PATENT DOCUMENTS

| | | |
|---|---|---|
| 4,034,743 A | 7/1977 | Greenwood et al. |
| 4,036,217 A | 7/1977 | Ito et al. |
| 4,053,951 A | 10/1977 | Hudspeth et al. |
| 4,090,513 A | 5/1978 | Togawa |
| 4,112,931 A | 9/1978 | Burns |
| 4,187,842 A | 2/1980 | Schreiber |
| 4,215,409 A | 7/1980 | Strowe |
| 4,241,739 A | 12/1980 | Elson |
| 4,258,718 A | 3/1981 | Goldman |
| 4,296,756 A | 10/1981 | Dunning et al. |
| 4,308,872 A | 1/1982 | Watson et al. |
| 4,323,064 A | 4/1982 | Hoenig et al. |
| 4,326,513 A | 4/1982 | Schulz et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,440,177 A | 4/1984 | Anderson et al. |
| 4,444,201 A | 4/1984 | Itoh |
| 4,463,764 A | 8/1984 | Anderson et al. |
| 4,473,081 A | 9/1984 | Dioguardi et al. |
| 4,495,944 A | 1/1985 | Brisson et al. |
| 4,537,190 A | 8/1985 | Caillot et al. |
| 4,550,726 A | 11/1985 | McEwen |
| 4,579,115 A | 4/1986 | Wallroth et al. |
| 4,637,385 A | 1/1987 | Rusz |
| 4,654,029 A | 3/1987 | D'Antonio |
| 4,736,750 A | 4/1988 | Valdespino et al. |
| 4,790,327 A | 12/1988 | Despotis |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,876,903 A | 10/1989 | Budinger |
| 4,917,108 A | 4/1990 | Mault |
| 4,984,158 A | 1/1991 | Hillsman |
| 4,990,894 A | 2/1991 | Loescher et al. |
| 5,003,985 A | 4/1991 | White et al. |
| 5,004,472 A | 4/1991 | Wallace |
| 5,009,662 A | 4/1991 | Wallace et al. |
| 5,020,527 A | 6/1991 | Dessertine |
| 5,021,046 A | 6/1991 | Wallace |
| 5,057,822 A | 10/1991 | Hoffman |
| 5,058,601 A | 10/1991 | Riker |
| 5,137,026 A | 8/1992 | Waterson et al. |
| 5,163,423 A | 11/1992 | Suzuki |
| 5,167,506 A | 12/1992 | Kilis et al. |
| 5,203,343 A | 4/1993 | Axe et al. |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,246,010 A | 9/1993 | Gazzara et al. |
| 5,251,632 A | 10/1993 | Delpy |
| 5,261,397 A | 11/1993 | Grunstein |
| 5,261,415 A | 11/1993 | Dussault |
| 5,277,195 A | 1/1994 | Williams |
| 5,279,304 A | 1/1994 | Einhorn et al. |
| 5,293,875 A | 3/1994 | Stone |
| 5,303,698 A | 4/1994 | Tobia et al. |
| 5,303,699 A | 4/1994 | Bonassa et al. |
| 5,307,795 A | 5/1994 | Whitwam et al. |
| 5,319,355 A | 6/1994 | Russek |
| 5,333,106 A | 7/1994 | Lanpher et al. |
| 5,339,825 A | 8/1994 | McNaughton et al. |
| 5,355,893 A | 10/1994 | Mick et al. |
| 5,357,975 A | 10/1994 | Kraemer et al. |
| 5,363,842 A | 11/1994 | Mishelevich et al. |
| 5,365,922 A | 11/1994 | Raemer |
| 5,373,851 A | 12/1994 | Reinhold, Jr. et al. |
| 5,383,470 A | 1/1995 | Kolbly |
| 5,402,796 A | 4/1995 | Packer et al. |
| 5,404,871 A | 4/1995 | Goodman et al. |
| 5,442,940 A | 8/1995 | Secker et al. |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,464,410 A | 11/1995 | Skeens et al. |
| 5,479,939 A | 1/1996 | Ogino |
| 5,487,731 A | 1/1996 | Denton |
| 5,495,848 A | 3/1996 | Aylsworth et al. |
| 5,501,231 A | 3/1996 | Kaish |
| 5,507,291 A | 4/1996 | Stirbl et al. |
| 5,517,985 A | 5/1996 | Kirk et al. |
| 5,518,002 A | 5/1996 | Wolf et al. |
| 5,534,851 A | 7/1996 | Russek |
| 5,537,992 A | 7/1996 | Bjoernstijerna et al. |
| 5,542,410 A | 8/1996 | Goodman et al. |
| 5,548,702 A * | 8/1996 | Li et al. ............... 715/769 |
| 5,549,117 A | 8/1996 | Tacklind et al. |
| 5,553,620 A | 9/1996 | Snider |
| 5,558,086 A | 9/1996 | Smith et al. |
| 5,560,353 A | 10/1996 | Willemot et al. |
| 5,564,414 A | 10/1996 | Walker et al. |
| 5,564,432 A | 10/1996 | Thomson |
| 5,571,142 A | 11/1996 | Brown et al. |
| 5,575,283 A | 11/1996 | Sjoestrand |
| 5,582,167 A | 12/1996 | Joseph |
| 5,590,648 A | 1/1997 | Mitchell et al. |
| 5,591,130 A | 1/1997 | Denton |
| 5,596,984 A | 1/1997 | O'Mahony et al. |
| 5,606,976 A | 3/1997 | Marshall |
| 5,611,335 A | 3/1997 | Makhoul et al. |
| 5,626,144 A | 5/1997 | Tacklind et al. |
| 5,632,281 A | 5/1997 | Rayburn |
| 5,634,461 A | 6/1997 | Faithfull et al. |
| 5,634,471 A | 6/1997 | Fairfax et al. |
| 5,642,735 A | 7/1997 | Kolbly |
| 5,647,346 A | 7/1997 | Holscher |
| 5,651,264 A | 7/1997 | Lo et al. |
| 5,655,516 A | 8/1997 | Goodman et al. |
| 5,660,168 A | 8/1997 | Ottosson et al. |
| 5,669,379 A | 9/1997 | Somerson et al. |
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |
| 5,692,497 A | 12/1997 | Schnitzer et al. |
| 5,697,959 A | 12/1997 | Poore |
| 5,704,346 A | 1/1998 | Inoue |
| 5,704,366 A | 1/1998 | Tacklind et al. |
| 5,704,367 A | 1/1998 | Ishikawa et al. |
| 5,706,801 A | 1/1998 | Remes et al. |
| 5,724,990 A | 3/1998 | Ogino |
| 5,730,140 A | 3/1998 | Fitch |
| 5,730,145 A | 3/1998 | Defares et al. |
| 5,735,287 A | 4/1998 | Thomson |
| 5,736,974 A * | 4/1998 | Selker ............... 715/862 |
| 5,738,092 A | 4/1998 | Mock et al. |
| 5,740,792 A | 4/1998 | Ashley et al. |
| 5,743,267 A | 4/1998 | Nikolic et al. |
| 5,752,506 A | 5/1998 | Richardson |
| 5,752,509 A | 5/1998 | Lachmann et al. |
| 5,755,218 A | 5/1998 | Johansson et al. |
| 5,758,652 A | 6/1998 | Nikolic |
| 5,778,874 A | 7/1998 | Maguire et al. |
| 5,794,612 A | 8/1998 | Wachter et al. |
| 5,800,361 A | 9/1998 | Rayburn |
| 5,806,514 A | 9/1998 | Mock et al. |
| 5,809,997 A | 9/1998 | Wolf |
| 5,813,397 A | 9/1998 | Goodman et al. |
| 5,819,723 A | 10/1998 | Joseph |
| 5,822,715 A | 10/1998 | Worthington et al. |
| 5,826,570 A | 10/1998 | Goodman et al. |
| 5,827,179 A | 10/1998 | Lichter et al. |
| 5,839,430 A | 11/1998 | Cama |
| 5,865,171 A | 2/1999 | Cinquin |
| 5,865,174 A | 2/1999 | Kloeppel |
| 5,875,777 A | 3/1999 | Eriksson |
| 5,878,744 A | 3/1999 | Pfeiffer |
| 5,881,723 A | 3/1999 | Wallace |
| 5,884,622 A | 3/1999 | Younes |
| 5,891,023 A | 4/1999 | Lynn |
| 5,899,203 A | 5/1999 | Defares et al. |
| 5,915,379 A | 6/1999 | Wallace |

| | | | |
|---|---|---|---|
| 5,915,380 A | 6/1999 | Wallace |
| 5,921,920 A | 7/1999 | Marshall et al. |
| 5,924,418 A | 7/1999 | Lewis |
| 5,931,160 A | 8/1999 | Gilmore |
| 5,932,812 A | 8/1999 | Delsing |
| 5,937,854 A | 8/1999 | Stenzler |
| 5,956,501 A | 9/1999 | Brown |
| 5,957,861 A | 9/1999 | Combs et al. |
| 5,971,937 A | 10/1999 | Ekstrom |
| 5,975,081 A | 11/1999 | Hood |
| 5,979,440 A | 11/1999 | Honkonen et al. |
| 5,980,466 A | 11/1999 | Thomson |
| 6,012,450 A | 1/2000 | Rubsamen |
| 6,017,315 A | 1/2000 | Starr |
| 6,024,089 A | 2/2000 | Wallace |
| 6,026,323 A | 2/2000 | Skladnev et al. |
| 6,032,119 A | 2/2000 | Brown et al. |
| 6,055,506 A | 4/2000 | Frasca, Jr. |
| 6,073,110 A | 6/2000 | Rhodes et al. |
| 6,099,481 A | 8/2000 | Daniels et al. |
| 6,106,481 A | 8/2000 | Cohen |
| 6,118,847 A | 9/2000 | Hernandez-Guerra |
| 6,119,684 A | 9/2000 | Nohl et al. |
| 6,148,814 A | 11/2000 | Clemmer et al. |
| 6,148,815 A | 11/2000 | Wolf |
| 6,155,257 A | 12/2000 | Lurie et al. |
| 6,158,432 A | 12/2000 | Biondi |
| 6,159,147 A | 12/2000 | Lichter et al. |
| 6,162,183 A | 12/2000 | Hoover |
| 6,167,362 A | 12/2000 | Brown et al. |
| 6,168,568 B1 | 1/2001 | Gavriely |
| 6,171,264 B1 | 1/2001 | Bader |
| 6,176,833 B1 | 1/2001 | Thomson |
| 6,186,956 B1 | 2/2001 | McNamee |
| 6,190,326 B1 | 2/2001 | McKinnon et al. |
| 6,192,876 B1 | 2/2001 | Denyer et al. |
| 6,198,963 B1 | 3/2001 | Haim et al. |
| 6,199,550 B1 | 3/2001 | Wiesmann et al. |
| 6,202,642 B1 | 3/2001 | McKinnon et al. |
| 6,213,955 B1 | 4/2001 | Karakasoglu et al. |
| 6,223,744 B1 | 5/2001 | Garon |
| 6,224,553 B1 | 5/2001 | Nevo |
| 6,233,539 B1 | 5/2001 | Brown |
| 6,234,963 B1 | 5/2001 | Blike et al. |
| 6,240,920 B1 | 6/2001 | Strom |
| 6,251,082 B1 | 6/2001 | Rayburn |
| 6,261,238 B1 | 7/2001 | Gavriely |
| 6,269,810 B1 | 8/2001 | Brooker et al. |
| 6,269,812 B1 | 8/2001 | Wallace |
| 6,273,088 B1 | 8/2001 | Hillsman |
| 6,279,574 B1 | 8/2001 | Richardson et al. |
| 6,283,923 B1 | 9/2001 | Finkelstein et al. |
| 6,287,264 B1 | 9/2001 | Hoffman |
| 6,301,497 B1 | 10/2001 | Neustadter |
| 6,302,106 B1 | 10/2001 | Lewis |
| 6,305,373 B1 | 10/2001 | Wallace |
| 6,322,502 B1 | 11/2001 | Schoenberg et al. |
| 6,339,410 B1 | 1/2002 | Milner |
| 6,340,348 B1 | 1/2002 | Krishnan |
| 6,342,040 B1 | 1/2002 | Starr |
| 6,349,722 B1 | 2/2002 | Gradon et al. |
| 6,349,724 B1 | 2/2002 | Burton et al. |
| 6,355,002 B1 | 3/2002 | Faram et al. |
| 6,360,745 B1 | 3/2002 | Wallace |
| 6,362,620 B1 | 3/2002 | Debbins |
| 6,367,475 B1 | 4/2002 | Kofoed et al. |
| 6,369,838 B1 | 4/2002 | Wallace |
| 6,370,419 B1 | 4/2002 | Lampotang |
| 6,377,046 B1 | 4/2002 | Debbins |
| 6,379,301 B1 | 4/2002 | Worthington et al. |
| 6,390,088 B1 | 5/2002 | Nohl et al. |
| 6,390,091 B1 | 5/2002 | Banner et al. |
| 6,390,092 B1 | 5/2002 | Leenhoven |
| 6,390,977 B1 | 5/2002 | Faithfull et al. |
| 6,402,698 B1 | 6/2002 | Mault |
| 6,408,043 B1 | 6/2002 | Hu |
| 6,415,792 B1 | 7/2002 | Schoolman |
| 6,416,471 B1 | 7/2002 | Kumar et al. |
| 6,421,650 B1 | 7/2002 | Goetz et al. |
| 6,427,687 B1 | 8/2002 | Kirk |
| 6,435,175 B1 | 8/2002 | Stenzler |
| 6,436,053 B1 | 8/2002 | Knapp, II et al. |
| 6,450,164 B1 | 9/2002 | Banner et al. |
| 6,454,708 B1 | 9/2002 | Ferguson et al. |
| 6,459,933 B1 | 10/2002 | Lurie et al. |
| 6,463,930 B2 | 10/2002 | Biondi et al. |
| 6,471,658 B1 | 10/2002 | Daniels et al. |
| 6,488,029 B1 | 12/2002 | Hood et al. |
| 6,488,629 B1 | 12/2002 | Saetre |
| RE37,970 E | 1/2003 | Costello, Jr. |
| 6,511,426 B1 | 1/2003 | Hossack |
| 6,512,938 B2 | 1/2003 | Claure |
| 6,515,683 B1 | 2/2003 | Wright |
| 6,517,497 B2 | 2/2003 | Rymut et al. |
| 6,533,723 B1 | 3/2003 | Lockery |
| 6,533,730 B2 | 3/2003 | Strom |
| 6,543,449 B1 | 4/2003 | Woodring |
| 6,543,701 B1 | 4/2003 | Ho |
| 6,544,192 B2 | 4/2003 | Starr |
| 6,547,728 B1 | 4/2003 | Cornuejols |
| 6,553,992 B1 | 4/2003 | Berthon-Jones et al. |
| 6,557,554 B1 | 5/2003 | Sugiura |
| 6,566,875 B1 | 5/2003 | Hasson |
| 6,571,122 B2 | 5/2003 | Schroeppel et al. |
| 6,571,796 B2 | 6/2003 | Banner et al. |
| 6,578,575 B1 | 6/2003 | Jonson |
| 6,581,592 B1 | 6/2003 | Bathe et al. |
| 6,584,973 B1 | 7/2003 | Biondi |
| 6,597,939 B1 | 7/2003 | Lampotang |
| 6,599,252 B2 | 7/2003 | Starr |
| 6,603,494 B1 | 8/2003 | Banks |
| 6,606,993 B1 | 8/2003 | Wiesmann et al. |
| 6,620,106 B2 | 9/2003 | Mault |
| 6,621,917 B1 | 9/2003 | Vilser |
| 6,629,934 B2 | 10/2003 | Mault et al. |
| 6,630,176 B2 | 10/2003 | Li |
| 6,644,312 B2 | 11/2003 | Berthon-Jones et al. |
| 6,645,158 B2 | 11/2003 | Mault |
| 6,650,346 B1 | 11/2003 | Jaeger |
| 6,651,653 B1 | 11/2003 | Honkonen et al. |
| 6,656,129 B2 | 12/2003 | Niles et al. |
| 6,668,829 B2 | 12/2003 | Biondi |
| 6,671,529 B2 | 12/2003 | Claure |
| 6,673,018 B2 | 1/2004 | Friedman |
| 6,675,801 B2 | 1/2004 | Wallace |
| 6,679,258 B1 | 1/2004 | Strom |
| 6,681,764 B1 | 1/2004 | Honkonen et al. |
| 6,698,423 B1 | 3/2004 | Honkonen et al. |
| 6,707,476 B1 | 3/2004 | Hochstedler |
| 6,708,688 B1 | 3/2004 | Rubin et al. |
| 6,709,405 B2 | 3/2004 | Jonson |
| 6,712,762 B1 | 3/2004 | Lichter et al. |
| 6,718,975 B2 | 4/2004 | Blomberg |
| 6,725,077 B1 | 4/2004 | Balloni |
| 6,725,860 B2 | 4/2004 | Wallroth et al. |
| 6,733,449 B1 | 5/2004 | Krishnamurthy |
| 6,738,079 B1 | 5/2004 | Kellerman et al. |
| 6,740,046 B2 | 5/2004 | Knapp, II et al. |
| 6,743,172 B1 | 6/2004 | Blike |
| 6,744,374 B1 | 6/2004 | Kuenzner |
| 6,745,764 B2 | 6/2004 | Hickle |
| 6,755,193 B2 | 6/2004 | Berthon-Jones et al. |
| 6,755,787 B2 | 6/2004 | Hossack |
| 6,760,610 B2 | 7/2004 | Tschupp et al. |
| 6,776,159 B2 | 8/2004 | Pelerossi et al. |
| 6,782,888 B1 | 8/2004 | Friberg |
| 6,790,178 B1 | 9/2004 | Mault et al. |
| 6,792,066 B2 | 9/2004 | Harder |
| 6,796,305 B1 | 9/2004 | Banner et al. |
| 6,801,227 B2 | 10/2004 | Bocionek |
| 6,801,802 B2 | 10/2004 | Sitzman et al. |
| 6,805,118 B2 | 10/2004 | Brooker et al. |
| 6,807,965 B1 | 10/2004 | Hickle |
| 6,820,614 B2 | 11/2004 | Bonutti |
| 6,820,618 B2 | 11/2004 | Banner et al. |
| 6,822,223 B2 | 11/2004 | Davis |
| 6,824,520 B2 | 11/2004 | Orr et al. |
| 6,828,910 B2 | 12/2004 | VanRyzin et al. |

| | | | | | | |
|---|---|---|---|---|---|---|
| 6,830,046 B2 | 12/2004 | Blakley et al. | | 7,278,579 B2 | 10/2007 | Loffredo |
| 6,834,647 B2 | 12/2004 | Blair et al. | | 7,282,032 B2 | 10/2007 | Miller |
| 6,837,242 B2 | 1/2005 | Younes | | 7,285,090 B2 | 10/2007 | Stivoric et al. |
| 6,839,753 B2 | 1/2005 | Biondi | | 7,294,105 B1 | 11/2007 | Islam |
| 6,845,773 B2 | 1/2005 | Berthon-Jones et al. | | 7,294,112 B1 | 11/2007 | Dunlop |
| 6,858,006 B2 | 2/2005 | MacCarter et al. | | 7,298,280 B2 | 11/2007 | Voege et al. |
| 6,860,266 B2 | 3/2005 | Blike | | 7,300,418 B2 | 11/2007 | Zaleski |
| 6,866,629 B2 | 3/2005 | Bardy | | 7,303,680 B2 | 12/2007 | Connell |
| 6,893,397 B2 | 5/2005 | Bardy | | 7,308,550 B2 | 12/2007 | Cornett |
| 6,899,103 B1 | 5/2005 | Hood | | 7,310,551 B1 | 12/2007 | Koh et al. |
| 6,899,683 B2 | 5/2005 | Mault et al. | | 7,310,720 B2 | 12/2007 | Cornett |
| 6,899,684 B2 | 5/2005 | Mault et al. | | 7,311,665 B2 | 12/2007 | Hawthorne et al. |
| 6,910,481 B2 | 6/2005 | Kimmel et al. | | 7,314,451 B2 | 1/2008 | Halperin et al. |
| 6,921,369 B1 | 7/2005 | Gehrke et al. | | 7,316,231 B2 | 1/2008 | Hickle |
| 6,923,079 B1 | 8/2005 | Snibbe | | 7,318,808 B2 | 1/2008 | Tarassenko et al. |
| 6,931,269 B2 | 8/2005 | Terry | | 7,318,892 B2 | 1/2008 | Connell |
| 6,932,083 B2 | 8/2005 | Jones et al. | | 7,321,802 B2 | 1/2008 | Wasner et al. |
| 6,932,767 B2 | 8/2005 | Landry | | 7,322,352 B2 | 1/2008 | Minshull et al. |
| 6,947,780 B2 | 9/2005 | Scharf | | 7,322,937 B2 | 1/2008 | Blomberg et al. |
| 6,951,541 B2 | 10/2005 | Desmarais | | 7,331,340 B2 | 2/2008 | Barney |
| 6,954,702 B2 | 10/2005 | Pierry et al. | | 7,333,969 B2 | 2/2008 | Lee |
| 6,956,572 B2 | 10/2005 | Zaleski | | 7,334,578 B2 | 2/2008 | Biondi |
| 6,970,919 B1 | 11/2005 | Doi | | 7,343,916 B2 | 3/2008 | Biondi et al. |
| 6,976,958 B2 | 12/2005 | Quy | | 7,343,917 B2 | 3/2008 | Jones |
| 6,986,347 B2 | 1/2006 | Hickle | | 7,347,200 B2 | 3/2008 | Jones et al. |
| 6,997,185 B2 | 2/2006 | Han et al. | | 7,347,207 B2 | 3/2008 | Ahlmen et al. |
| 6,997,880 B2 | 2/2006 | Carlebach et al. | | 7,351,340 B2 | 4/2008 | Connel |
| 7,008,380 B1 | 3/2006 | Rees et al. | | 7,362,341 B2 | 4/2008 | McGuire et al. |
| 7,017,574 B2 | 3/2006 | Biondi | | 7,367,337 B2 | 5/2008 | Berthon-Jones et al. |
| 7,019,652 B2 | 3/2006 | Richardson | | 7,367,955 B2 | 5/2008 | Zhang et al. |
| 7,033,323 B2 | 4/2006 | Botbol et al. | | 7,369,757 B2 | 5/2008 | Farbarik |
| 7,036,504 B2 | 5/2006 | Wallace | | 7,374,535 B2 | 5/2008 | Schoenberg et al. |
| 7,039,878 B2 | 5/2006 | Auer | | 7,377,276 B2 | 5/2008 | Roy |
| 7,040,315 B1 | 5/2006 | Strömberg | | 7,380,210 B2 | 5/2008 | Lontka et al. |
| 7,040,318 B2 | 5/2006 | Däscher et al. | | RE40,365 E | 6/2008 | Kirchgeorg et al. |
| 7,040,321 B2 | 5/2006 | Göbel | | 7,383,148 B2 | 6/2008 | Ahmed |
| 7,046,254 B2 | 5/2006 | Brown et al. | | 7,387,610 B2 | 6/2008 | Stahmann et al. |
| 7,047,092 B2 | 5/2006 | Wimsatt | | 7,413,546 B2 | 8/2008 | Agutter et al. |
| 7,051,736 B2 | 5/2006 | Banner et al. | | 7,422,562 B2 | 9/2008 | Hatib et al. |
| 7,062,251 B2 | 6/2006 | Birkett | | 7,425,201 B2 | 9/2008 | Euliano et al. |
| 7,066,173 B2 | 6/2006 | Banner et al. | | 7,435,220 B2 | 10/2008 | Ranucci |
| 7,077,125 B2 | 7/2006 | Scheuch | | 7,438,072 B2 | 10/2008 | Izuchukwu |
| 7,081,091 B2 | 7/2006 | Merrett et al. | | 7,438,073 B2 | 10/2008 | Delache et al. |
| 7,081,095 B2 | 7/2006 | Lynn | | 7,448,383 B2 | 11/2008 | Delache et al. |
| 7,083,574 B2 | 8/2006 | Kline | | 7,452,333 B2 | 11/2008 | Roteliuk |
| 7,089,927 B2 | 8/2006 | John et al. | | 7,464,339 B2 | 12/2008 | Keenan, Jr. et al. |
| 7,089,937 B2 | 8/2006 | Berthon-Jones et al. | | 7,469,698 B1 | 12/2008 | Childers et al. |
| 7,094,208 B2 | 8/2006 | Williams et al. | | 7,487,774 B2 | 2/2009 | Acker |
| 7,116,810 B2 | 10/2006 | Miller et al. | | 7,490,085 B2 | 2/2009 | Walker |
| 7,117,438 B2 * | 10/2006 | Wallace et al. ............... 715/709 | | 7,496,400 B2 | 2/2009 | Hoskonen et al. |
| 7,128,578 B2 | 10/2006 | Lampotang | | 7,500,481 B2 | 3/2009 | Delache et al. |
| 7,137,074 B1 | 11/2006 | Newton et al. | | 7,504,954 B2 | 3/2009 | Spaeder |
| 7,147,600 B2 | 12/2006 | Bardy | | 7,512,450 B2 | 3/2009 | Ahmed |
| 7,156,808 B2 | 1/2007 | Quy | | 7,512,593 B2 | 3/2009 | Karklins et al. |
| 7,162,296 B2 | 1/2007 | Leonhardt et al. | | 7,527,053 B2 | 5/2009 | DeVries et al. |
| 7,164,972 B2 | 1/2007 | Imhof et al. | | 7,527,054 B2 | 5/2009 | Misholi |
| 7,165,221 B2 | 1/2007 | Monteleone | | 7,530,353 B2 | 5/2009 | Choncholas et al. |
| 7,169,112 B2 | 1/2007 | Caldwell | | RE40,806 E | 6/2009 | Gradon et al. |
| 7,172,557 B1 | 2/2007 | Parker | | 7,543,582 B2 | 6/2009 | Lu et al. |
| 7,182,083 B2 | 2/2007 | Yanof et al. | | 7,548,833 B2 | 6/2009 | Ahmed |
| 7,187,790 B2 | 3/2007 | Sabol | | 7,552,731 B2 | 6/2009 | Jorczak et al. |
| 7,188,621 B2 | 3/2007 | DeVries | | 7,556,036 B2 | 7/2009 | Bouillon et al. |
| 7,201,734 B2 | 4/2007 | Hickle | | 7,559,903 B2 | 7/2009 | Moussavi et al. |
| 7,203,353 B2 | 4/2007 | Klotz | | 7,562,657 B2 | 7/2009 | Blanch et al. |
| 7,210,478 B2 | 5/2007 | Banner et al. | | 7,565,905 B2 | 7/2009 | Hickle |
| 7,211,049 B2 | 5/2007 | Bradley et al. | | 7,584,712 B2 | 9/2009 | Lu |
| 7,219,666 B2 | 5/2007 | Friberg et al. | | 7,590,551 B2 | 9/2009 | Saleh |
| 7,220,230 B2 | 5/2007 | Roteliuk et al. | | 7,597,099 B2 | 10/2009 | Jones et al. |
| 7,222,054 B2 | 5/2007 | Geva | | 7,603,170 B2 | 10/2009 | Hatlestad et al. |
| 7,223,965 B2 | 5/2007 | Davis | | 7,603,631 B2 | 10/2009 | Bermudez et al. |
| 7,228,323 B2 | 6/2007 | Angerer et al. | | 7,606,668 B2 | 10/2009 | Pierry et al. |
| 7,241,269 B2 | 7/2007 | McCawley et al. | | 7,609,138 B2 | 10/2009 | Dietrich et al. |
| 7,246,618 B2 | 7/2007 | Habashi | | 7,610,915 B2 | 11/2009 | Dittmann |
| 7,247,154 B2 | 7/2007 | Hickle | | 7,618,378 B2 | 11/2009 | Bingham et al. |
| 7,252,640 B2 | 8/2007 | Ni et al. | | 7,625,345 B2 | 12/2009 | Quinn |
| 7,261,690 B2 | 8/2007 | Teller et al. | | 7,630,755 B2 | 12/2009 | Stahmann et al. |
| 7,264,730 B2 | 9/2007 | Connell | | 7,650,181 B2 | 1/2010 | Freeman et al. |
| 7,270,126 B2 | 9/2007 | Wallace | | 7,652,571 B2 | 1/2010 | Parkulo et al. |
| 7,275,540 B2 | 10/2007 | Bolam et al. | | 7,654,966 B2 | 2/2010 | Westinskow et al. |

| Patent/Pub No. | Date | Name |
|---|---|---|
| 7,658,188 B2 | 2/2010 | Halpern et al. |
| 7,662,106 B2 | 2/2010 | Daniels et al. |
| 7,668,579 B2 | 2/2010 | Lynn |
| 7,669,598 B2 | 3/2010 | Rick et al. |
| 7,671,733 B2 | 3/2010 | McNeal et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,698,156 B2 | 4/2010 | Martucci et al. |
| 7,708,015 B2 | 5/2010 | Seeger et al. |
| 7,717,112 B2 | 5/2010 | Sun et al. |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,778,709 B2 | 8/2010 | Gollasch et al. |
| 7,778,851 B2 | 8/2010 | Schoenberg et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,659 B2 | 9/2010 | Breen |
| 7,793,660 B2 | 9/2010 | Kimmel et al. |
| 7,810,497 B2 | 10/2010 | Pittman et al. |
| 7,814,906 B2 | 10/2010 | Moretti |
| 7,819,815 B2 | 10/2010 | Younes |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,866,317 B2 | 1/2011 | Muellinger et al. |
| 7,871,394 B2 | 1/2011 | Halbert et al. |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,895,527 B2 | 2/2011 | Zaleski et al. |
| 7,909,033 B2 | 3/2011 | Faram |
| 7,912,537 B2 | 3/2011 | Lee et al. |
| 7,927,286 B2 | 4/2011 | Ranucci |
| 7,931,601 B2 | 4/2011 | Ranucci |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,970,450 B2 | 6/2011 | Kroecker et al. |
| 7,990,251 B1 | 8/2011 | Ford, Jr. |
| 2001/0056358 A1 | 12/2001 | Dulong |
| 2002/0026941 A1 | 3/2002 | Biondi et al. |
| 2002/0044059 A1 | 4/2002 | Reeder |
| 2002/0077863 A1 | 6/2002 | Rutledge |
| 2002/0091548 A1 | 7/2002 | Auer |
| 2002/0171682 A1* | 11/2002 | Frank et al. ............... 345/790 |
| 2002/0177758 A1 | 11/2002 | Schoenberg et al. |
| 2003/0060723 A1 | 3/2003 | Joo et al. |
| 2003/0062045 A1* | 4/2003 | Woodring et al. ....... 128/204.18 |
| 2003/0106553 A1 | 6/2003 | Vanderveen |
| 2003/0130567 A1 | 7/2003 | Mault et al. |
| 2003/0130595 A1 | 7/2003 | Mault |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0142138 A1* | 7/2003 | Brown et al. ............... 345/797 |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0208152 A1 | 11/2003 | Avrahami et al. |
| 2003/0208465 A1 | 11/2003 | Yurko |
| 2003/0222548 A1 | 12/2003 | Richardson et al. |
| 2003/0230308 A1 | 12/2003 | Linden |
| 2004/0010425 A1 | 1/2004 | Wilkes et al. |
| 2004/0021693 A1 | 2/2004 | Monteleone |
| 2004/0034289 A1 | 2/2004 | Teller et al. |
| 2004/0059604 A1 | 3/2004 | Zaleski |
| 2004/0073453 A1 | 4/2004 | Nenov |
| 2004/0078231 A1 | 4/2004 | Wilkes et al. |
| 2004/0121767 A1 | 6/2004 | Simpson et al. |
| 2004/0122294 A1 | 6/2004 | Hatlestad et al. |
| 2004/0150525 A1 | 8/2004 | Wilson |
| 2004/0167465 A1 | 8/2004 | Mihai et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0224293 A1 | 11/2004 | Penning |
| 2004/0236240 A1 | 11/2004 | Kraus et al. |
| 2004/0249673 A1 | 12/2004 | Smith |
| 2005/0016534 A1 | 1/2005 | Ost |
| 2005/0033198 A1 | 2/2005 | Kehyayan et al. |
| 2005/0054910 A1 | 3/2005 | Tremblay et al. |
| 2005/0055242 A1 | 3/2005 | Bello et al. |
| 2005/0055244 A1 | 3/2005 | Mullan et al. |
| 2005/0065817 A1 | 3/2005 | Mihai et al. |
| 2005/0075542 A1 | 4/2005 | Goldreich |
| 2005/0075904 A1 | 4/2005 | Wager |
| 2005/0085869 A1 | 4/2005 | Tehrani |
| 2005/0104860 A1 | 5/2005 | McCreary |
| 2005/0108057 A1 | 5/2005 | Cohen |
| 2005/0112013 A1 | 5/2005 | DeVries et al. |
| 2005/0112325 A1 | 5/2005 | Hickle |
| 2005/0124866 A1 | 6/2005 | Elaz |
| 2005/0133027 A1 | 6/2005 | Elaz |
| 2005/0137480 A1 | 6/2005 | Alt et al. |
| 2005/0139213 A1 | 6/2005 | Blike |
| 2005/0143632 A1 | 6/2005 | Elaz |
| 2005/0156933 A1 | 7/2005 | Lee et al. |
| 2005/0171876 A1 | 8/2005 | Golden |
| 2005/0177096 A1 | 8/2005 | Bollish et al. |
| 2005/0188083 A1 | 8/2005 | Biondi |
| 2005/0192488 A1 | 9/2005 | Bryenton et al. |
| 2005/0204310 A1 | 9/2005 | De Zwart et al. |
| 2005/0215904 A1 | 9/2005 | Sumanaweera |
| 2005/0217674 A1 | 10/2005 | Burton et al. |
| 2005/0251040 A1 | 11/2005 | Relkuntwar |
| 2005/0288571 A1 | 12/2005 | Perkins |
| 2006/0047202 A1 | 3/2006 | Elliott |
| 2006/0078867 A1 | 4/2006 | Penny |
| 2006/0080140 A1 | 4/2006 | Buttner |
| 2006/0080343 A1 | 4/2006 | Carter |
| 2006/0102171 A1 | 5/2006 | Gavish |
| 2006/0122474 A1 | 6/2006 | Teller et al. |
| 2006/0129055 A1 | 6/2006 | Orr et al. |
| 2006/0144396 A1 | 7/2006 | DeVries |
| 2006/0149144 A1 | 7/2006 | Lynn et al. |
| 2006/0149589 A1 | 7/2006 | Wager |
| 2006/0150982 A1 | 7/2006 | Wood |
| 2006/0155183 A1 | 7/2006 | Kroecker |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0173257 A1 | 8/2006 | Nagai et al. |
| 2006/0174884 A1 | 8/2006 | Habashi |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn |
| 2006/0196507 A1 | 9/2006 | Bradley |
| 2006/0200009 A1 | 9/2006 | Wekell et al. |
| 2006/0213518 A1 | 9/2006 | DeVries |
| 2006/0229822 A1 | 10/2006 | Theobald |
| 2006/0235324 A1 | 10/2006 | Lynn |
| 2006/0237015 A1 | 10/2006 | Berthon-Jones et al. |

| | | | | | | |
|---|---|---|---|---|---|---|
| 2006/0249151 A1 | 11/2006 | Gambone | | 2008/0185009 A1 | 8/2008 | Choncholas |
| 2006/0249153 A1 | 11/2006 | DeVries et al. | | 2008/0205427 A1 | 8/2008 | Jost |
| 2006/0264762 A1 | 11/2006 | Starr | | 2008/0208012 A1 | 8/2008 | Ali |
| 2006/0278221 A1 | 12/2006 | Schermeier et al. | | 2008/0214947 A1 | 9/2008 | Hunt |
| 2006/0278222 A1 | 12/2006 | Schermeier et al. | | 2008/0230057 A1 | 9/2008 | Sutherland |
| 2006/0293609 A1 | 12/2006 | Stahmann et al. | | 2008/0236582 A1 | 10/2008 | Tehrani |
| 2006/0294464 A1 | 12/2006 | Tokimoto et al. | | 2008/0236585 A1 | 10/2008 | Parker |
| 2007/0000490 A1 | 1/2007 | DeVries | | 2008/0243016 A1 | 10/2008 | Liao et al. |
| 2007/0000494 A1 | 1/2007 | Banner et al. | | 2008/0251070 A1 | 10/2008 | Pinskiy |
| 2007/0016441 A1 | 1/2007 | Stroup | | 2008/0255880 A1 | 10/2008 | Beller |
| 2007/0017515 A1 | 1/2007 | Wallace | | 2008/0258929 A1 | 10/2008 | Maschke |
| 2007/0021673 A1 | 1/2007 | Arbel et al. | | 2008/0270912 A1 | 10/2008 | Booth |
| 2007/0028921 A1 | 2/2007 | Banner et al. | | 2008/0281219 A1 | 11/2008 | Glickman et al. |
| 2007/0038081 A1 | 2/2007 | Eck et al. | | 2008/0293025 A1 | 11/2008 | Zamierowsi |
| 2007/0060812 A1 | 3/2007 | Harel et al. | | 2008/0295830 A1 | 12/2008 | Martonen |
| 2007/0062532 A1 | 3/2007 | Choncholas | | 2008/0295839 A1 | 12/2008 | Habashi |
| 2007/0062533 A1 | 3/2007 | Choncholas et al. | | 2008/0306351 A1 | 12/2008 | Izumi |
| 2007/0073181 A1 | 3/2007 | Pu | | 2008/0308109 A1 | 12/2008 | Brain |
| 2007/0113849 A1 | 5/2007 | Matthews | | 2008/0312954 A1 | 12/2008 | Ullrich |
| 2007/0119453 A1 | 5/2007 | Lu et al. | | 2008/0319513 A1 | 12/2008 | Pu |
| 2007/0123758 A1 | 5/2007 | Miesel et al. | | 2009/0005651 A1 | 1/2009 | Ward |
| 2007/0123792 A1 | 5/2007 | Kline | | 2009/0007909 A1 | 1/2009 | Carrico |
| 2007/0129647 A1 | 6/2007 | Lynn | | 2009/0038921 A1 | 2/2009 | Kaps et al. |
| 2007/0149860 A1 | 6/2007 | Lynn et al. | | 2009/0054743 A1 | 2/2009 | Stewart |
| 2007/0156060 A1 | 7/2007 | Cervantes | | 2009/0055735 A1 | 2/2009 | Zaleski |
| 2007/0156456 A1 | 7/2007 | McGillin | | 2009/0062725 A1 | 3/2009 | Goebel |
| 2007/0157931 A1 | 7/2007 | Parker | | 2009/0063181 A1 | 3/2009 | Nho |
| 2007/0163589 A1 | 7/2007 | DeVries | | 2009/0065004 A1 | 3/2009 | Childers et al. |
| 2007/0179357 A1 | 8/2007 | Bardy | | 2009/0076342 A1 | 3/2009 | Amurthur et al. |
| 2007/0185390 A1 | 8/2007 | Perkins et al. | | 2009/0124917 A1 | 5/2009 | Hatlestad et al. |
| 2007/0191697 A1 | 8/2007 | Lynn et al. | | 2009/0125333 A1 | 5/2009 | Heywood |
| 2007/0199566 A1 | 8/2007 | Be'eri | | 2009/0126734 A1 | 5/2009 | Dunsmore |
| 2007/0208438 A1 | 9/2007 | El-Mankabady et al. | | 2009/0131758 A1 | 5/2009 | Heywood |
| 2007/0215155 A1 | 9/2007 | Marx et al. | | 2009/0133701 A1 | 5/2009 | Brain |
| 2007/0225574 A1 | 9/2007 | Ueda | | 2009/0143694 A1 | 6/2009 | Krauss et al. |
| 2007/0229249 A1 | 10/2007 | McNeal | | 2009/0145438 A1 | 6/2009 | Brain |
| 2007/0241884 A1 | 10/2007 | Yamazaki | | 2009/0149200 A1 | 6/2009 | Jayasinghe |
| 2007/0265510 A1 | 11/2007 | Bardy | | 2009/0149723 A1 | 6/2009 | Krauss et al. |
| 2007/0265877 A1 | 11/2007 | Rice et al. | | 2009/0149743 A1 | 6/2009 | Barron et al. |
| 2007/0271122 A1 | 11/2007 | Zaleski | | 2009/0149927 A1 | 6/2009 | Kneuer |
| 2007/0272241 A1 | 11/2007 | Sanborn | | 2009/0150184 A1 | 6/2009 | Spahn |
| 2007/0272242 A1 | 11/2007 | Sanborn | | 2009/0171167 A1 | 7/2009 | Baker, Jr. |
| 2007/0273216 A1 | 11/2007 | Farbarik | | 2009/0192421 A1 | 7/2009 | Huster et al. |
| 2007/0276439 A1 | 11/2007 | Miesel et al. | | 2009/0209828 A1 | 8/2009 | Musin |
| 2007/0293741 A1 | 12/2007 | Bardy | | 2009/0209849 A1 | 8/2009 | Rowe |
| 2008/0000477 A1 | 1/2008 | Huster et al. | | 2009/0216145 A1 | 8/2009 | Skerl et al. |
| 2008/0000479 A1 | 1/2008 | Elaz | | 2009/0221926 A1 | 9/2009 | Younes |
| 2008/0007396 A1 | 1/2008 | Parkulo | | 2009/0240523 A1 | 9/2009 | Friedlander |
| 2008/0022215 A1 | 1/2008 | Lee et al. | | 2009/0241952 A1 | 10/2009 | Nicolazzi |
| 2008/0033661 A1 | 2/2008 | Syroid et al. | | 2009/0241956 A1 | 10/2009 | Baker, Jr. |
| 2008/0039735 A1 | 2/2008 | Hickerson | | 2009/0241957 A1 | 10/2009 | Baker, Jr. |
| 2008/0041380 A1 | 2/2008 | Wallace | | 2009/0241958 A1 | 10/2009 | Baker, Jr. |
| 2008/0045844 A1 | 2/2008 | Arbel et al. | | 2009/0244003 A1 | 10/2009 | Bonnat |
| 2008/0047554 A1 | 2/2008 | Roy | | 2009/0249247 A1 | 10/2009 | Tseng et al. |
| 2008/0053438 A1 | 3/2008 | DeVries | | 2009/0250054 A1 | 10/2009 | Loncar |
| 2008/0064963 A1 | 3/2008 | Schwaibold et al. | | 2010/0004517 A1 | 1/2010 | Bryenton et al. |
| 2008/0065420 A1 | 3/2008 | Tirinato | | 2010/0022904 A1 | 1/2010 | Centen |
| 2008/0066753 A1 | 3/2008 | Martin et al. | | 2010/0030092 A1 | 2/2010 | Kristensen et al. |
| 2008/0072896 A1 | 3/2008 | Setzer | | 2010/0048985 A1 | 2/2010 | Henke et al. |
| 2008/0072900 A1 | 3/2008 | Kenyon et al. | | 2010/0048986 A1 | 2/2010 | Henke et al. |
| 2008/0072901 A1 | 3/2008 | Habashi | | 2010/0049034 A1 | 2/2010 | Eck et al. |
| 2008/0072902 A1 | 3/2008 | Setzer | | 2010/0049264 A1 | 2/2010 | Henke et al. |
| 2008/0076970 A1 | 3/2008 | Foulis et al. | | 2010/0049265 A1 | 2/2010 | Henke et al. |
| 2008/0077033 A1 | 3/2008 | Figueiredo | | 2010/0056852 A1 | 3/2010 | Henke et al. |
| 2008/0077038 A1 | 3/2008 | McDonough et al. | | 2010/0056853 A1 | 3/2010 | Henke et al. |
| 2008/0077436 A1 | 3/2008 | Muradia | | 2010/0056855 A1 | 3/2010 | Henke et al. |
| 2008/0078390 A1 | 4/2008 | Milne | | 2010/0056929 A1 | 3/2010 | Stahmann et al. |
| 2008/0086691 A1 | 4/2008 | Hopermann et al. | | 2010/0056941 A1 | 3/2010 | Henke et al. |
| 2008/0091122 A1 | 4/2008 | Dunlop | | 2010/0056942 A1 | 3/2010 | Henke et al. |
| 2008/0092043 A1 | 4/2008 | Trethewey | | 2010/0057148 A1 | 3/2010 | Henke et al. |
| 2008/0103368 A1 | 5/2008 | Craine et al. | | 2010/0059061 A1 | 3/2010 | Brain |
| 2008/0110460 A1 | 5/2008 | Elaz | | 2010/0063348 A1 | 3/2010 | Henke et al. |
| 2008/0125873 A1 | 5/2008 | Payne | | 2010/0063350 A1 | 3/2010 | Henke et al. |
| 2008/0154100 A1 | 6/2008 | Thalmeier et al. | | 2010/0063365 A1 | 3/2010 | Pisani et al. |
| 2008/0161653 A1 | 7/2008 | Lin et al. | | 2010/0069774 A1 | 3/2010 | Bingham et al. |
| 2008/0172249 A1 | 7/2008 | Glaser-Seidnitzer | | 2010/0072055 A1 | 3/2010 | Tanaka et al. |
| 2008/0178880 A1 | 7/2008 | Christopher | | 2010/0076278 A1 | 3/2010 | van der Zande et al. |
| 2008/0178882 A1 | 7/2008 | Christopher | | 2010/0081890 A1 | 4/2010 | Li et al. |
| 2008/0183057 A1 | 7/2008 | Taube | | 2010/0083968 A1 | 4/2010 | Wondka et al. |

| Publication No. | Date | Inventor(s) |
|---|---|---|
| 2010/0095961 A1 | 4/2010 | Tornesel et al. |
| 2010/0130873 A1 | 5/2010 | Yuen et al. |
| 2010/0160839 A1 | 6/2010 | Freeman et al. |
| 2010/0274100 A1 | 10/2010 | Behar et al. |
| 2010/0298718 A1 | 11/2010 | Gilham et al. |
| 2010/0312132 A1 | 12/2010 | Wood et al. |
| 2010/0317980 A1 | 12/2010 | Guglielmino |
| 2011/0004489 A1 | 1/2011 | Schoenberg et al. |
| 2011/0009746 A1 | 1/2011 | Tran et al. |
| 2011/0015493 A1 | 1/2011 | Koschek |
| 2011/0041849 A1 | 2/2011 | Chen et al. |
| 2011/0054289 A1 | 3/2011 | Derchak et al. |
| 2011/0055720 A1 | 3/2011 | Potter et al. |
| 2011/0098638 A1 | 4/2011 | Chawla et al. |
| 2011/0126151 A1 | 5/2011 | Bean et al. |
| 2011/0138308 A1 | 6/2011 | Palmer et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0154241 A1 | 6/2011 | Skidmore et al. |
| 2012/0030611 A1 | 2/2012 | Skidmore |
| 2012/0066609 A1 | 3/2012 | Howard et al. |

FOREIGN PATENT DOCUMENTS

| | | |
|---|---|---|
| EP | 1374938 | 1/2004 |
| EP | 1421966 | 5/2004 |
| EP | 1464357 | 10/2004 |
| GB | 2319967 | 6/1998 |
| WO | WO9014852 A1 | 12/1990 |
| WO | WO9308534 A1 | 4/1993 |
| WO | WO9312823 A2 | 7/1993 |
| WO | WO9314696 A1 | 8/1993 |
| WO | WO9414374 A1 | 7/1994 |
| WO | WO9508471 A1 | 3/1995 |
| WO | WO9532480 A1 | 11/1995 |
| WO | WO9624285 A1 | 8/1996 |
| WO | WO9720592 A1 | 6/1997 |
| WO | WO9811840 A1 | 3/1998 |
| WO | WO9814116 A2 | 4/1998 |
| WO | WO9829790 A2 | 7/1998 |
| WO | WO9833554 A1 | 8/1998 |
| WO | WO9840014 A1 | 9/1998 |
| WO | WO9841267 A1 | 9/1998 |
| WO | WO9841267 C1 | 9/1998 |
| WO | WO9841269 A1 | 9/1998 |
| WO | WO9841270 A1 | 9/1998 |
| WO | WO9841271 A1 | 9/1998 |
| WO | WO9858219 A1 | 12/1998 |
| WO | WO9903524 A1 | 1/1999 |
| WO | WO9952431 A1 | 10/1999 |
| WO | WO9952437 A1 | 10/1999 |
| WO | WO9959460 A2 | 11/1999 |
| WO | WO9962403 A1 | 12/1999 |
| WO | WO0018293 A1 | 4/2000 |
| WO | WO0019886 A1 | 4/2000 |
| WO | WO0062664 A1 | 10/2000 |
| WO | WO0100264 A1 | 1/2001 |
| WO | WO0100265 A1 | 1/2001 |
| WO | WO0128416 A1 | 4/2001 |
| WO | WO0134022 A1 | 5/2001 |
| WO | WO0245566 A2 | 6/2002 |
| WO | WO02082967 A2 | 10/2002 |
| WO | WO03015005 A2 | 2/2003 |
| WO | WO03024317 A2 | 3/2003 |
| WO | WO03045493 A2 | 6/2003 |
| WO | WO03053503 A1 | 7/2003 |
| WO | WO03060650 A2 | 7/2003 |
| WO | WO03060651 A2 | 7/2003 |
| WO | WO03075989 A2 | 9/2003 |
| WO | WO03075990 A2 | 9/2003 |
| WO | WO03075991 A1 | 9/2003 |
| WO | WO03084405 A2 | 10/2003 |
| WO | WO2004014216 A2 | 2/2004 |
| WO | WO2004014226 A1 | 2/2004 |
| WO | WO2004032719 A2 | 4/2004 |
| WO | WO2004043254 A1 | 5/2004 |
| WO | WO2005010796 | 2/2005 |
| WO | WO2005024729 A1 | 3/2005 |
| WO | WO2005055825 A1 | 6/2005 |
| WO | WO2005056087 A1 | 6/2005 |
| WO | WO2005069740 A2 | 8/2005 |
| WO | WO2005077260 A1 | 8/2005 |
| WO | WO2005112739 A1 | 12/2005 |
| WO | WO2006008745 A2 | 1/2006 |
| WO | WO2006009830 A2 | 1/2006 |
| WO | WO2006037184 A2 | 4/2006 |
| WO | WO2006050388 A2 | 5/2006 |
| WO | WO2006051466 A1 | 5/2006 |
| WO | WO2006078432 A2 | 7/2006 |
| WO | WO2006094055 A2 | 9/2006 |
| WO | WO2006096080 A1 | 9/2006 |
| WO | WO2006109072 A2 | 10/2006 |
| WO | WO2006123956 A1 | 11/2006 |
| WO | WO2006125986 A1 | 11/2006 |
| WO | WO2006125987 A1 | 11/2006 |
| WO | WO2006125989 A1 | 11/2006 |
| WO | WO2006125990 A1 | 11/2006 |
| WO | WO2006137067 A2 | 12/2006 |
| WO | WO2007033050 A2 | 3/2007 |
| WO | WO2007106804 A2 | 9/2007 |
| WO | WO2007145948 | 12/2007 |
| WO | WO2008030091 A1 | 3/2008 |
| WO | WO2008042699 A2 | 4/2008 |
| WO | WO2008058997 A2 | 5/2008 |
| WO | WO2008062554 A1 | 5/2008 |
| WO | WO2008113410 A1 | 9/2008 |
| WO | WO2008118951 A1 | 10/2008 |
| WO | WO2008140528 A1 | 11/2008 |
| WO | WO2008146264 A2 | 12/2008 |
| WO | WO2008148134 A1 | 12/2008 |
| WO | WO2009024967 A2 | 2/2009 |
| WO | WO2009027864 A1 | 3/2009 |
| WO | WO2009036334 A1 | 3/2009 |
| WO | WO2009124297 A1 | 10/2009 |
| WO | WO2010009531 A1 | 1/2010 |
| WO | WO2010020980 A1 | 2/2010 |
| WO | WO2010021730 A1 | 2/2010 |
| WO | WO2010039989 A1 | 4/2010 |
| WO | WO2010126916 A1 | 11/2010 |
| WO | WO2010141415 A1 | 12/2010 |
| WO | WO2011005953 A2 | 1/2011 |
| WO | WO2011022242 A1 | 2/2011 |

OTHER PUBLICATIONS

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

PCT International Search Report and Written Opinion in Application PCT/US2010/058131, mailed May 18, 2011, 12 pgs.

PCT International Search Report and Written Opinion in Application PCT/US2010/058132, mailed Mar. 3, 2011, 10 pgs.

PCT International Search Report mailed Apr. 7, 2011, International Application No. PCT/US2010/060871, International Filing Date Dec. 16, 2010, Applicant Nellcor Puritan Bennett LLC, 3 pgs.

U.S. Appl. No. 12/631,685, Office Action mailed Nov. 15, 2011, 22 pgs.

U.S. Appl. No. 12/631,685, Office Action mailed Feb. 29, 2012, 23 pgs.

U.S. Appl. No. 12/631,712, Office Action mailed Nov. 14, 2011, 20 pgs.

U.S. Appl. No. 12/631,712, Office Action mailed Feb. 29, 2012, 22 pgs.

U.S. Appl. No. 12/631,750, Office Action mailed Dec. 8, 2011, 12 pgs.

U.S. Appl. No. 12/760,649, Office Action mailed Jan. 6, 2012, 11 pgs.

U.S. Appl. No. 12/970,696, Office Action mailed Aug. 2, 2012, 12 pgs.

U.S. Appl. No. 12/631,685, Advisory Action mailed May 11, 2012, 3 pgs.
U.S. Appl. No. 12/631,712, Advisory Action mailed May 11, 2012, 3 pgs.
U.S. Appl. No. 12/631,750, Advisory Action mailed Jul. 24, 2012, 3 pgs.
U.S. Appl. No. 12/631,750, Office Action mailed May 16, 2012, 13 pgs.
U.S. Appl. No. 12/760,649, Office Action mailed Jul. 20, 2012, 13 pgs.
US 7,284,551, 10/2007, Jones et al. (withdrawn)

* cited by examiner

VISUAL INDICATION OF SETTINGS CHANGES ON A VENTILATOR GRAPHICAL USER INTERFACE

RELATED APPLICATIONS

This application is related to co-owned U.S. patent application Ser. No. 12/631,712, entitled "Display of Respiratory Data on a Ventilator Graphical User Interface," filed Dec. 4, 2009; U.S. patent application Ser. No. 12/631,750, entitled "Display and Access to Settings on a Respiratory Ventilator Graphical User Interface," filed Dec. 4, 2009; U.S. patent application Ser. No. 12/631,685, entitled "Visual Indication of Alarms on a Ventilator Graphical User Interface," filed Dec. 4, 2009; and U.S. patent application Ser. No. 12/760,649, entitled "Quick Initiation of Respiratory Support via a Ventilator User Interface," filed Apr. 15, 2010; the entire disclosures of all of which are hereby incorporated herein by reference.

INTRODUCTION

A ventilator is a device that mechanically helps patients breathe by replacing some or all of the muscular effort required to inflate and deflate the lungs. During ventilation, the ventilator may be configured to display useful information to the clinician and to receive inputs and commands from the clinician via one or more user interfaces, including a graphical user interface (GUI). The inputs and commands may include, inter alia, settings inputs during initial ventilator setup or changes to ventilatory settings during ventilation.

Due to the complexity of ventilators, it may be difficult for a clinician to identify where changes to ventilator settings may be entered or edited. Further, it may be difficult for a clinician to identify settings information on multiple screens and displays of the GUI. Specifically, it may be difficult for a clinician to determine whether, how, and where a settings change was implemented on the GUI. For instance, a clinician may wish to undo a settings change, such as when the settings change adversely impacted ventilatory treatment or failed to have the desired affect, and the clinician may need to quickly and easily identify an appropriate access screen on the GUI for adjusting and/or deleting the settings change. A clinician may also desire continued access to ventilatory settings while viewing and monitoring a display of respiratory data.

Visual Indication of Settings Changes on a Ventilator Graphical User Interface This disclosure describes improved systems and methods for visualizing the application of changes to respiratory settings in a ventilatory system. Specifically, the present disclosure provides for a setup animation window that may be easily accessed from a setup icon, for example, and also provides for a settings animation window that may be easily accessed from any number of displayed ventilatory settings. In fact, the setup animation window may be directly accessed by touching, clicking, or otherwise selecting the setup icon and may expand from the setup icon to display any number of settings access elements, Alternatively, the settings animation window may be directly accessed by touching, clicking, or otherwise selecting any one of the displayed ventilatory settings and may expand from the displayed ventilatory settings to provide corresponding settings access elements. The corresponding settings access elements each corresponding to an individual ventilatory setting of the displayed ventilatory settings and useful for efficiently adjusting the displayed ventilatory settings. Ventilatory settings may be changed and accepted via either animation window. Further, upon accepting settings changes from the settings animation window, settings may appear to visually float or fade into the displayed ventilatory settings. In this embodiment, clinicians may view the settings changes as they are accepted and applied to the GUI.

Additionally, the setup and the settings animation windows may include a transparency feature whereby the animation windows may be viewed simultaneously with other data displayed on the GUI, or other user interface. The animation windows may be configured to "time out," or automatically close, when input has not been received within a predetermined time period. Alternatively, the animation windows may include a pin-up feature whereby an animation window may remain open unless and until a clinician desires to close the animation window.

Specifically, embodiments recite a graphical user interface for displaying a setup animation window including access elements for changing ventilatory settings. The graphical user interface may comprise at least one window associated with the graphical user interface and one or more elements within the at least one window. The one or more elements may further comprise one or more actual ventilatory settings and a setup icon. The setup icon may be selectable such that selection of the setup icon initiates display of the setup animation window. Display of the setup animation window may expand from the setup icon. The setup animation window may further comprise one or more settings access elements, a transparency icon, and a pin-up icon. The one or more settings access elements may be arranged in a same configuration as the one or more actual ventilatory settings. Upon selection of the transparency icon, a transparency of the setup animation window may be adjusted such that graphical data displayed within the at least one window may be simultaneously viewable with the setup animation window. Upon selection of the pin-up icon, the setup animation window may be displayed until a close command is received. Upon accepting a pending setting value, the pending setting value may become a changed actual setting value and may populate a corresponding actual ventilatory setting of the plurality of actual ventilatory settings. Populating the corresponding actual ventilatory setting with the changed actual setting value may further comprise visually floating the plurality of settings access elements having actual settings values and the changed actual setting value from the settings animation window to corresponding actual ventilatory settings of the plurality of actual ventilatory settings.

Another embodiment may recite a graphical user interface for displaying a settings animation window including access elements for changing ventilatory settings. The graphical user interface may further comprise at least one window associated with the graphical user interface and one or more elements within the at least one window comprising a plurality of actual ventilatory settings. Selection of at least one of the plurality of actual ventilatory settings may initiate display of the settings animation window. The settings animation window may expand from the plurality of actual ventilatory settings and may further comprise a plurality of settings access elements and a transparency element. Upon selection of the transparency element, graphical data displayed in the at least one window may be simultaneously viewed with the settings animation window. Upon accepting a pending setting value, the pending setting value may become a changed actual setting value and may populate a corresponding actual ventilatory setting of the plurality of actual ventilatory settings. Populating the corresponding actual ventilatory setting with the changed actual setting value may further comprise visually floating the plurality of settings access elements having actual settings values and the changed actual setting value from the settings animation window to corresponding actual ventilatory settings of the plurality of actual ventilatory settings.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The patent or appliction file contains at least one drawing executed in color. Copies of this patent or patent application publication with color drawing(s) will be provied by the Office upon request and payment of the necessary fee.

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment having graphical user interfaces for configuring and changing settings.

This disclosure describes systems and methods for accessing and changing ventilatory settings. Specifically, embodiments may provide an animation window that is easily accessed from any number of displayed ventilatory settings. In fact, the animation window may expand from the displayed ventilatory settings and may provide a number of setting access elements, each corresponding to an individual ventilatory setting, for efficiently adjusting displayed ventilatory settings. Settings may be changed and accepted via the animation window and, upon acceptance, may appear to visually float into the displayed ventilatory settings. As such, clinicians may view the settings changes as they are accepted and applied to the GUI. Additionally, the animation window may include a transparency feature whereby the animation window may be viewed simultaneously with other data displayed on the GUI, or other user interface. The animation window may be configured to automatically close when input has not been received within a predetermined time period. Alternatively, the animation window may include a pin-up feature whereby the animation window may remain open unless and until a clinician desires to close the animation window.

Figure 1:
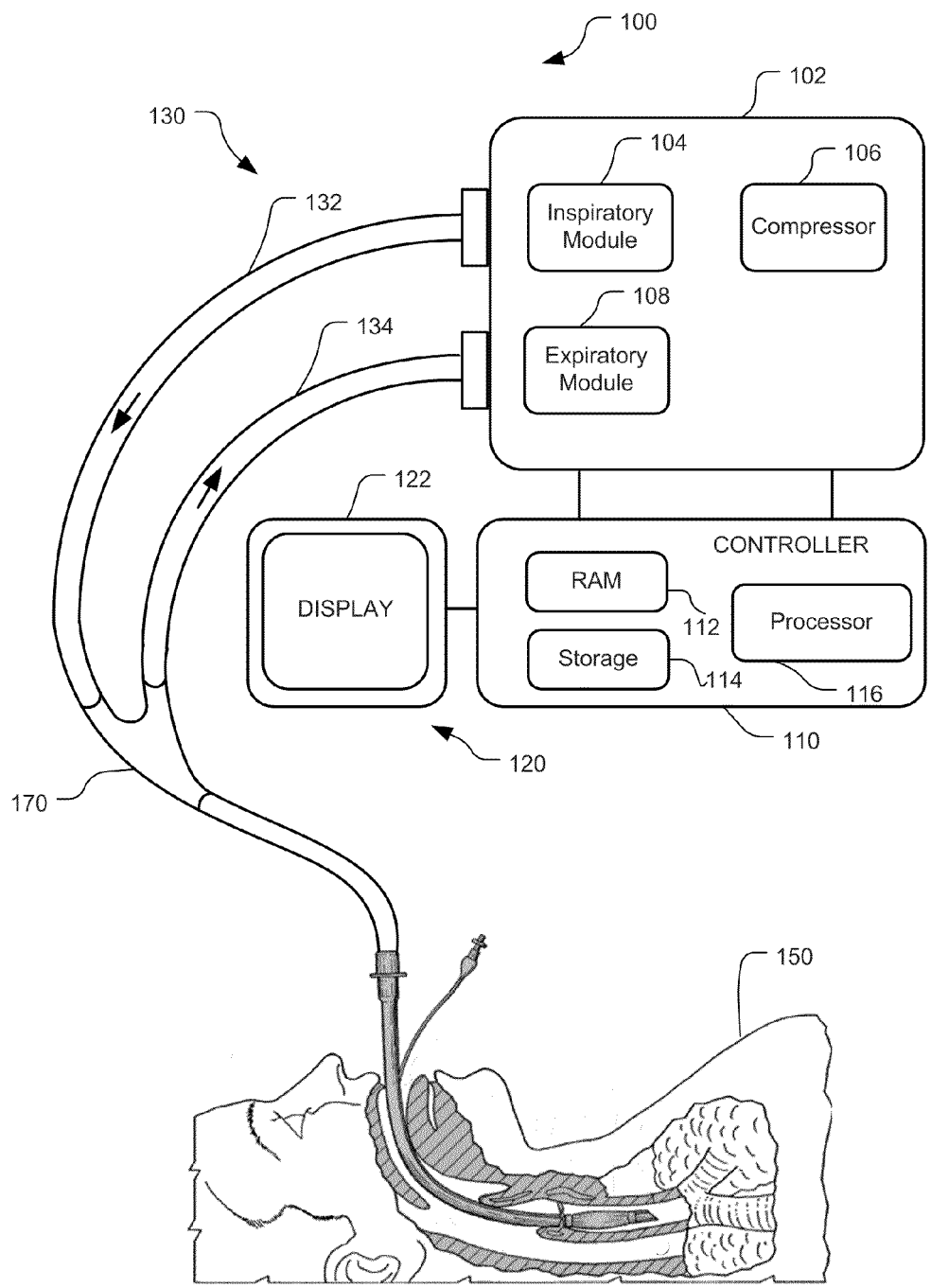
FIG. 1 is a diagram illustrating an embodiment of an exemplary ventilator connected to a human patient.

FIG. 1 illustrates an embodiment of a ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive patient interface.

Ventilation tubing system 130 may be a two-limb (shown) or a one-limb circuit for carrying gas to and from the patient 150. In a two-limb embodiment as shown, a fitting, typically referred to as a "wye-fitting" 170, may be provided to couple the patient interface to an inspiratory limb 132 and an expiratory limb 134 of the ventilation tubing system 130.

Pneumatic system 102 may be configured in a variety of ways. In the present example, system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 to provide a gas source for ventilatory support via inspiratory limb 132.

The pneumatic system may include a variety of other components, including sources for pressurized air and/or oxygen, mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., reset alarms, change ventilator settings, select operational modes, view monitored parameters, etc.). Controller 110 may include memory 112, one or more processors 116, storage 114, and/or other components of the type commonly found in command and control computing devices.

The memory 112 is computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 110 may monitor pneumatic system 102 in order to evaluate the condition of the patient and to ensure proper functioning of the ventilator according to respiratory settings. The specific monitoring may be based on settings inputs received from pneumatic system 102 and sensors, operator interface 120, and/or other components of the ventilator. In the depicted example, operator interface includes a display 122 that is touch-sensitive, enabling the display to serve both as an input and output device.

Figure 2:
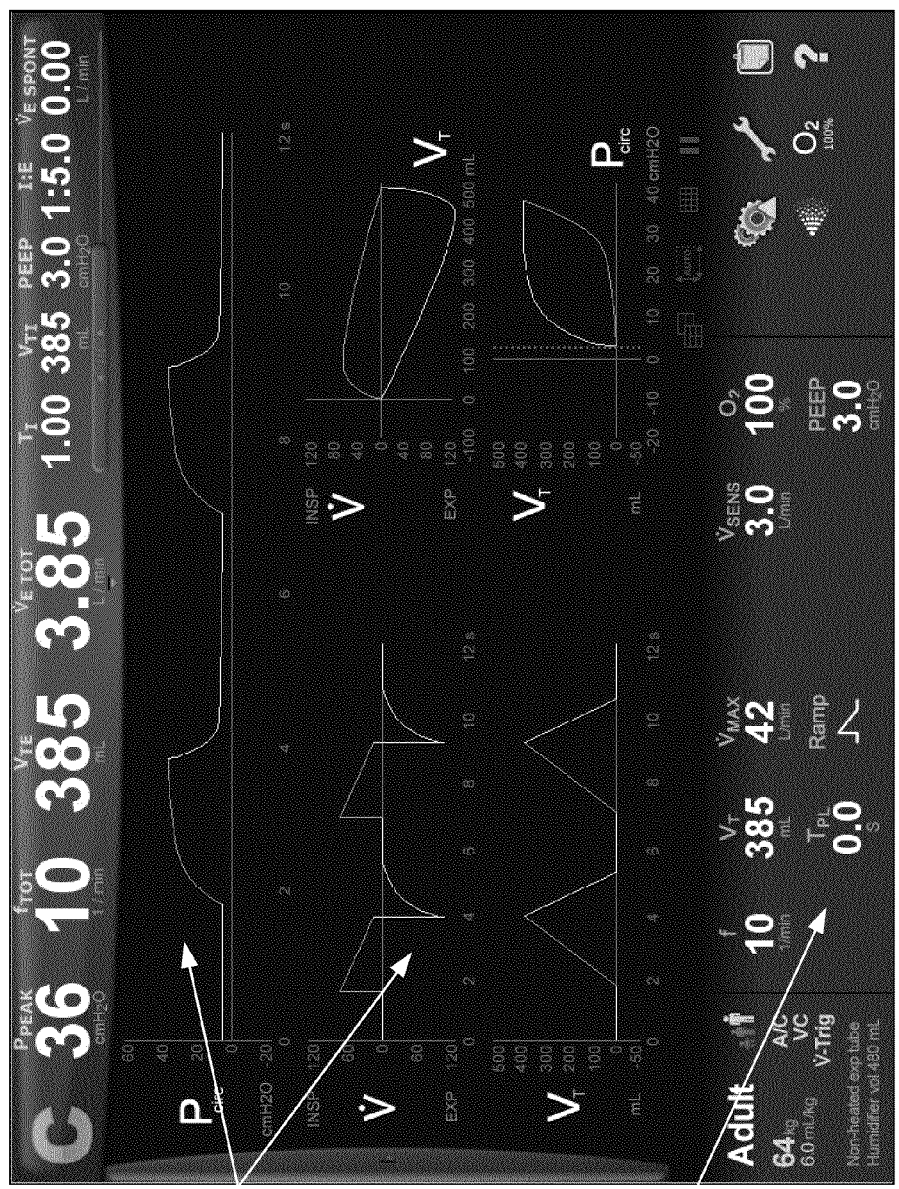
FIG. 2 is an illustration of an embodiment of a graphical user interface displaying graphical respiratory data and actual ventilatory settings.

FIG. 2 is an illustration of an embodiment of a graphical user interface displaying graphical respiratory data and actual respiratory settings.

For example, the graphical user interface (GUI) may display graphical respiratory data 202. Graphical respiratory data 202 may include, for instance, graphs, wave representations, pie graphs, or other suitable forms of graphical display. Examples of such graphic representations may include, but are not limited to, pressure waveforms, flow waveforms, flow-volume loops, pressure-volume loops, etc. Indeed, in keeping with the spirit of the present disclosure, any graphical or other data display that may be provided by the ventilator based on current respiratory settings may be displayed as graphical data 202.

In addition, the GUI may provide actual ventilatory settings 204. Actual ventilatory settings 204 may refer to any ventilatory setting applicable to the proper functioning of the ventilator and/or the appropriate monitoring of a patient. Actual ventilatory settings 204 may refer to those settings currently implemented by the ventilator. The GUI may be further configured to represent the actual ventilatory settings 204 in a particular font color such that a clinician may be alerted that the settings are being currently implemented by the ventilator. For example, the actual ventilatory settings 204 may be presented in a white font.

Actual ventilatory settings 204 may include settings for frequency, tidal volume, maximum and minimum flow, FiO2, PEEP, etc., as illustrated in FIG. 2. However, as noted above, actual ventilatory settings 204 may display any currently applied, or actual, ventilatory setting that may be useful to a clinician.

By way of example, actual ventilatory settings 204 may include a variety of settings for governing the proper delivery of ventilation to a patient. For example, a setting for frequency, f, may be provided (as illustrated, 10 breaths per minute). Frequency refers to a number of breaths over a period of time that should be delivered by the ventilator to the patient. By way of another example, a setting for tidal volume, $V_T$, may be provided (as illustrated, 385 mL). Tidal volume refers to the total volume of air inhaled and exhaled for one respiratory cycle. As such, the ventilator may be configured with a tidal volume setting to ensure that the patient receives and exhales an adequate volume of air. One or more settings for flow may also be provided (as illustrated, maximum flow set to 42 L/min). Flow refers to circuit airflow into and out of a patient's lungs and is governed by a pressure gradient between the lungs and the external atmospheric pressure. As very high flow may cause damage to a patient's lungs, trachea, etc., and an extremely low flow may indicate a leak or other unsafe condition, flow settings may include a maximum flow and a minimum flow, for example. A fractional inspired oxygen ($FiO_2$) setting may also be provided (as illustrated, 100%). $FiO_2$ refers to a percent of oxygen delivered to the patient, e.g., ranging from 21% (room air) to 100%. A setting for positive end-expiratory pressure (PEEP) may be included as well (as illustrated, 3.0 $H_2O$). During each breath, air is delivered by the ventilator to the patient's lungs, which results in a net increase in pressure (e.g., in cm $H_2O$). Pressure may be delivered from a non-zero baseline pressure, for instance, a baseline pressure above zero cm $H_2O$ is referred to as positive-end expiratory pressure or PEEP. When the ventilator includes a PEEP setting, the patient is prevented from exhaling to zero cm $H_2O$, or atmospheric pressure. Thus, PEEP increases the volume of air left in the lungs at the end of expiration.

The above-described ventilatory settings may be configured according to any suitable means, for instance according to safety standards, clinical studies, or other applicable protocols or specifications. Additionally, as will be described further herein, actual ventilatory settings 204 may be changed or adjusted based on the condition of the patient, or other considerations. Only a sampling of the illustrated actual ventilatory settings 204 have been defined and described, but the described ventilatory settings are characteristic of ventilatory settings that may be configured and displayed via actual ventilatory settings 204. As such, the above-described or illustrated ventilatory settings are not to be understood as an exclusive array, as any number of similar settings may be displayed for the clinician within the spirit of the present disclosure. Further, the described ventilatory settings are not to be understood as a necessary array, as any number of the described ventilatory settings may be appropriately replaced by other suitable ventilatory settings without departing from the spirit of the present disclosure.

Figure 3:
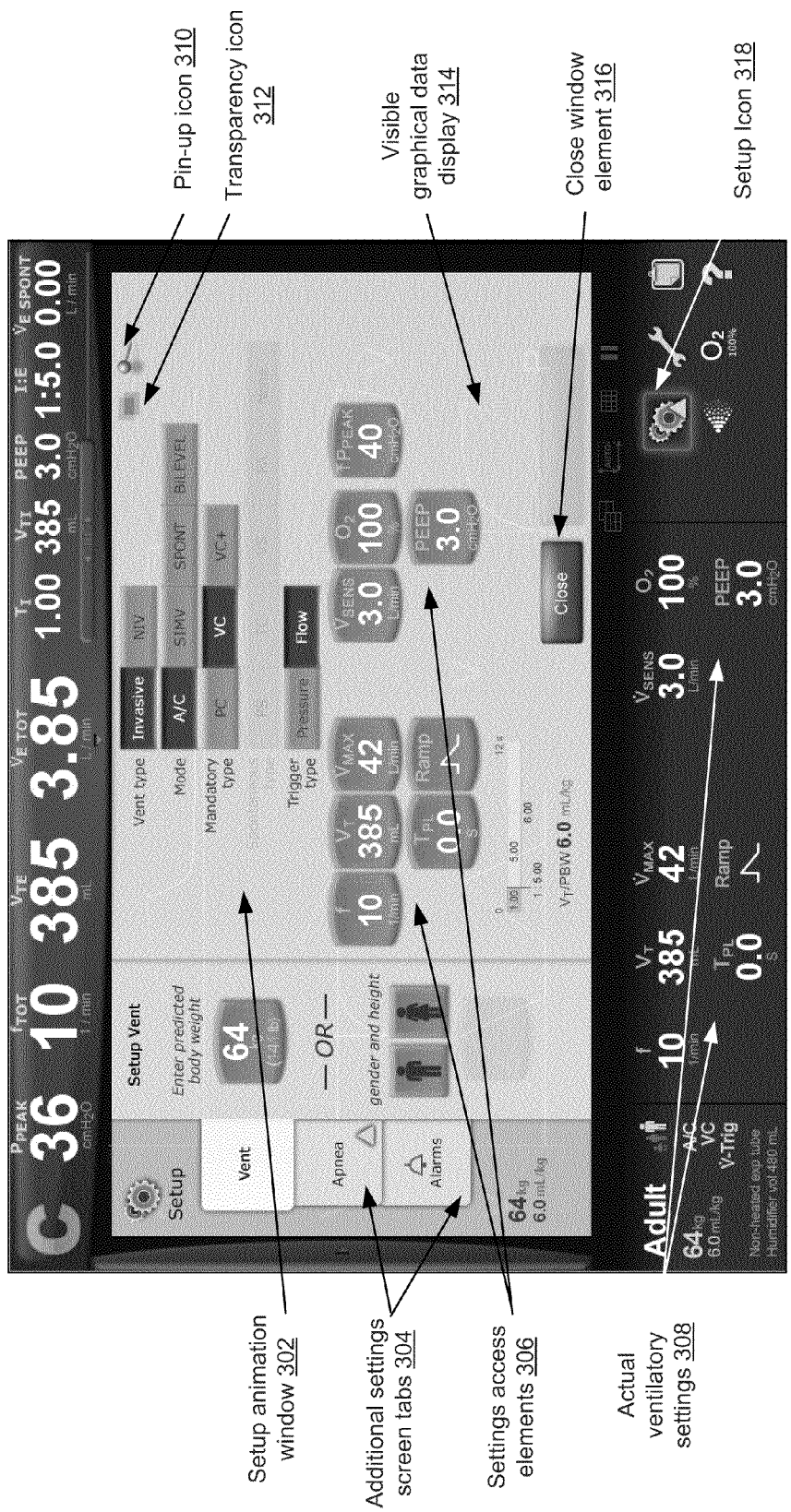
FIG. 3 is an illustration of an embodiment of a graphical user interface displaying a setup animation window for accessing and changing ventilatory settings.

FIG. 3 is an illustration of an embodiment of a graphical user interface displaying a setup animation window for accessing and changing ventilatory settings.

According to one embodiment, as illustrated in FIG. 3, a setup animation window 302 may be provided. Setup animation window 302 may be accessed by touching, clicking, or otherwise selecting an icon, such as setup icon 318, or any other setup access element. As described above, any suitable access method by which a clinician may logically and easily access setup animation window 302 may be provided in keeping with the present disclosure.

Setup animation window 302 may be displayed as a page, boxed window, or other suitable display. Further, when setup animation window 302 is accessed, it may appear to expand from setup icon 318, for instance. Alternatively, setup animation window 302 may be displayed as a pop-up window or it may expand from a border of the GUI, for instance. Setup animation window 302 may display a full setup window (as shown), enabling a clinician to access additional settings screens and elements, such as apnea and alarm settings screens (as illustrated by additional settings screen tabs 304). In another embodiment, as described further below with reference to FIG. 9, a settings animation window may be displayed, providing only settings elements corresponding to actual ventilatory settings 308 for instance. Indeed any suitable animation window may be displayed to a clinician such that the clinician may easily and efficiently access and change ventilatory settings.

As illustrated, animation window 302 may include settings access elements 306. A plurality of settings access elements 306 may be displayed as buttons, tabs, icons, or any other suitable visual access element. The settings access elements 306 may be configured in the same visual arrangement as the actual ventilatory settings 308, such that a clinician may easily correlate the actual ventilatory settings 308 with the settings access elements 306 provided for adjusting them. In addition, actual settings values associated with the actual ventilatory settings 308 may be initially displayed in settings access elements 306 (e.g., 10 breaths per min, 385 mL, eta). As such, actual settings values initially displayed in settings access elements 306 may be represented in a font color indicating that the values are actual settings values, for instance in a white font. Thereafter, upon display of animation window 302, a clinician may touch, click, or otherwise select one or more of the settings access elements 306 in order to input or change the displayed actual settings values. According to some embodiments, the setup animation window 302 may be displayed for a predetermined amount of time. The predetermined amount of time may be preconfigured by the manufacturer, or otherwise, such that display of the setup animation window 302 may "time out" or automatically close after the predetermined amount of time if no settings have been selected or changed. According to another embodiment of the present disclosure, a pin-up feature for the setup animation window 302 may be provided. For example, by touching, clicking, or otherwise selecting a pin-up icon 310, the setup animation window 302 may be displayed until the clinician desires to "un-pin" or close the setup animation window 302. In this case, the setup animation window 302 will not "time out," but will continue to be displayed to the clinician. For example, during a training session wherein the setup screen may be viewed and discussed, a pin-up feature may be desirable. Alternatively, a clinician may wish to change a setting, and then observe the effect of that change on the ventilatory treatment. The clinician may not want the setup animation window 302 to time out such that the setting may be easily undone or additionally adjusted.

According to still other embodiments, a transparency feature may be associated with the setup animation window 302. For example, by touching, clicking or otherwise selecting a transparency element, for instance transparency icon 312, a clinician may adjust the transparency and/or opacity of the setup animation window 302. As such, the clinician may adjust the setup animation window 302 to be highly transparent such that graphical respiratory data may be simultaneously viewed with the setup animation window 302. This feature may be appropriate in combination with the pin-up feature such that the clinician may both view relevant respiratory data and have immediate access to ventilatory settings. In the alternative, a clinician may adjust the setup animation window 302 to be highly opaque such that displayed graphical data may not detract from viewing the setup animation window 302. Alternatively still, the setup animation window 302 may be adjusted to balance transparency and opacity such that both relevant respiratory data and the setup animation window 302 may be easily viewed. For example, the transparency feature is illustrated in FIG. 3 such that graphical data display 314 is visible while the setup animation window 302 is open. Indeed, graphical data display 314 appears to be displayed behind the setup animation window 302. In order to optimize the display of both setup animation window 302 and graphical data display 314, textual data, such as scalar data, coordinates, axis labels, etc., may be faded out. Alternatively, actual waveforms, curves, and/or loops may be displayed without fading.

Setup animation window 302 may also provide a close window element 316. Close element 316 may be displayed upon accessing setup animation window 302. When no changes to ventilatory settings have been made, close element 316 may be displayed until setup animation window 302 times out or, if the setup animation window 302 is pinned, until such time as the clinician desires to close setup animation window 302.

In other embodiments, after changes have been made to the ventilatory settings, additional elements may be provided for accepting or saving the settings changes (not shown). Further, upon accepting changes to the ventilatory settings, setup animation window 302 may automatically close and actual ventilatory settings 308 may be automatically populated with the accepted changed settings values. Additionally or alternatively, upon accepting changes to the ventilatory settings, setup animation window 302 may appear to fade away and the settings values of settings access elements 306 may appear to float or fade down and populate the actual ventilatory settings 308. That is, all actual or pending settings values displayed in settings access elements 306, whether settings changes were made or not, may appear to visually populate actual ventilatory settings 308. Thus, a visual indication of the settings changes as they are applied to actual ventilatory settings on the GUI is provided for the clinician.

As described above, a setup icon 318 may also be provided within the GUI. As described above, the setup icon 318 may be selected for accessing setup animation window 302. Upon selection, setup icon 318 may further be displayed as focused. As such, setup icon 318 may offer a visual indication whenever ventilatory settings are being accessed or changed by the clinician via setup animation window 302.

Figure 4:
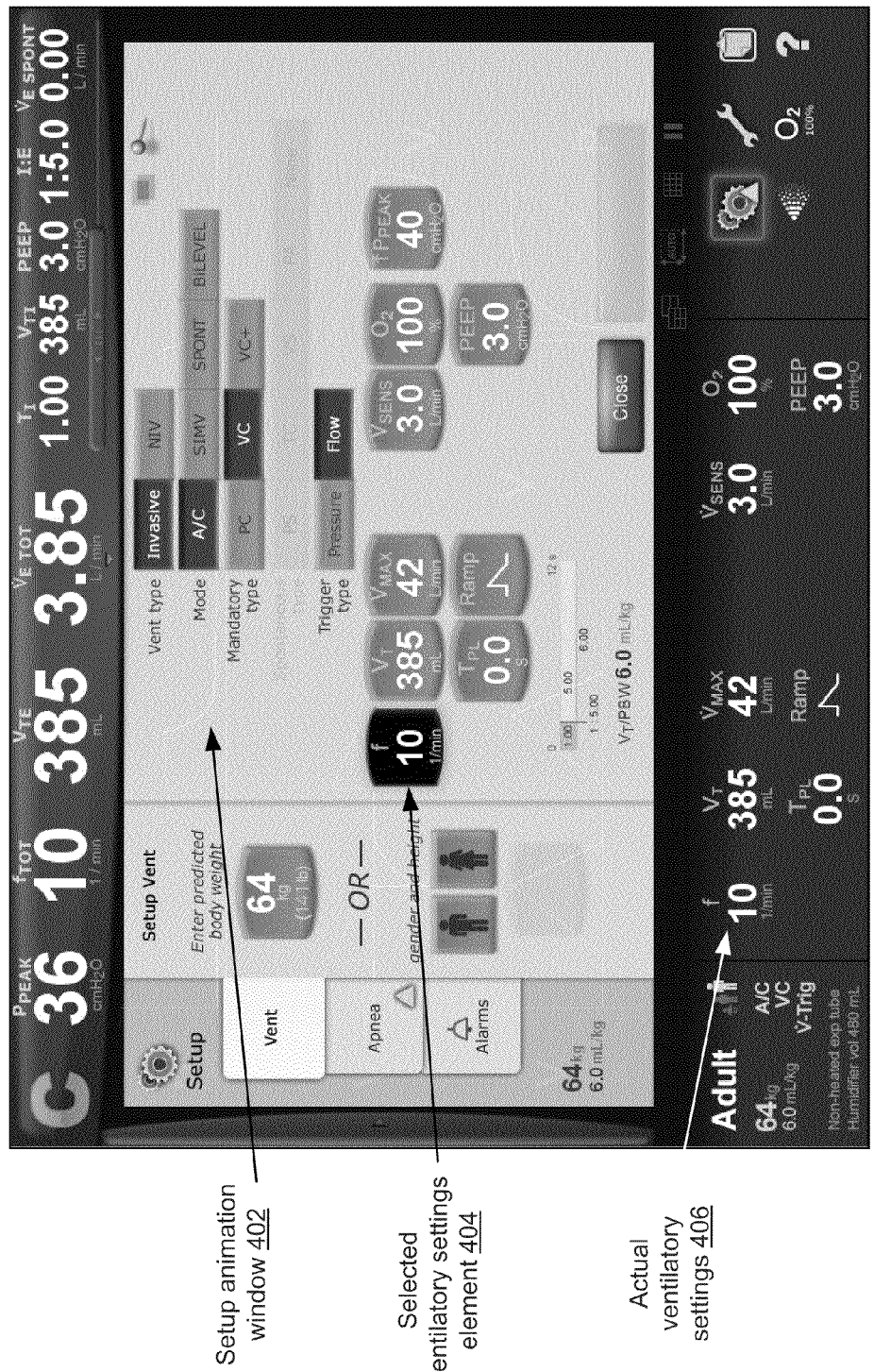
FIG. 4 is an illustration of an embodiment of a graphical user interface displaying a selected ventilatory setting element on the setup animation window.

FIG. 4 is an illustration of an embodiment of a graphical user interface displaying a selected ventilatory setting element on the setup animation window.

As described above, setup animation window 402 may be accessed via a settings icon, for instance. The setup animation window 402 may then provide a clinician with access to one or more ventilatory settings elements. The one or more ventilatory settings elements may display actual settings values corresponding to actual settings values displayed in actual ventilatory settings 406, for instance. Thereafter, a clinician may select an individual ventilatory setting element, for example selected ventilatory setting element 404, for adjustment. The selected ventilatory setting element 404 may be identified by creation of a visual indication of selection, highlighting for example, such that it may be differentiated from unselected access elements.

According to the illustrated embodiment, although a setting element may be selected, the settings value associated with that setting element may remain the actual ventilatory setting value until it is changed. For example, the actual frequency setting value, i.e., 10 breaths/min, represented as the actual frequency setting of actual ventilatory settings 406, may be reproduced in selected ventilatory settings element 404 unless and until the frequency setting is changed. As such, in the illustrated embodiment, selected ventilator), settings element 404 includes a settings value of 10 breaths/min in a white font, indicating an actual status for the frequency setting value unless and until it is changed.

Figure 5:
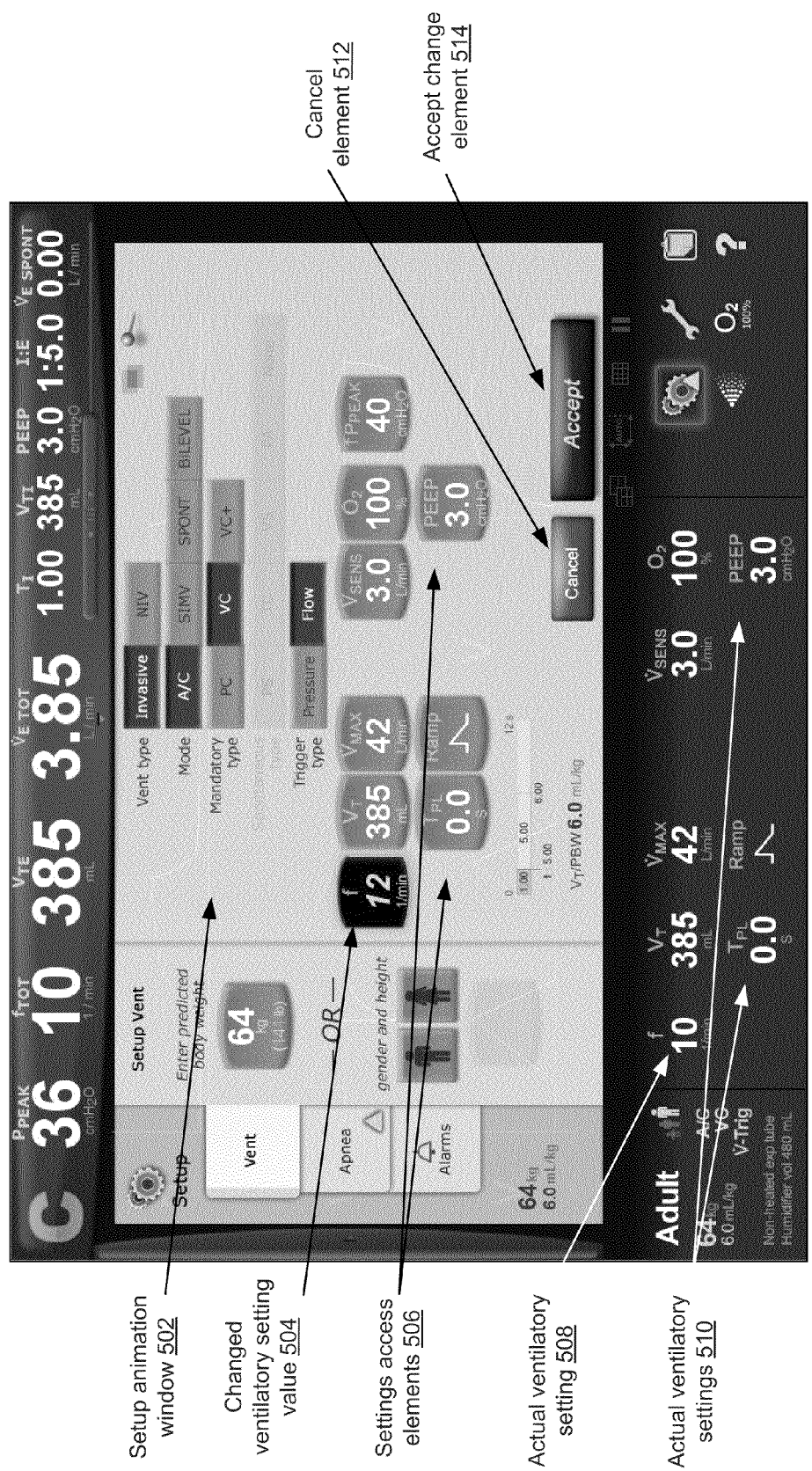
FIG. 5 is an illustration of an embodiment of a graphical user interface displaying a change to the setting value of the selected ventilatory setting element on the setup animation window.

FIG. 5 is an illustration of an embodiment of a graphical user interface displaying a change to the setting value of the selected ventilatory setting element on the setup animation window.

As illustrated in FIG. 5, the setting value of the selected ventilatory setting element 404 (as described in FIG. 4) has been changed from a frequency of 10 breaths/min to a frequency of 12 breaths/min in setup animation window 502. Settings may be changed via any suitable means, for instance, via direct input into a settings input field, via use of a scroll wheel, thumbwheel, knob, mouse, or scroll bar for adjusting settings up and down, or via any other suitable device. Thus, FIG. 5 illustrates changed ventilatory setting value 504 as 12 breaths/min. Changed ventilatory setting value 504 may also be represented in a different font to indicate that the changed setting value has a pending status, rather than an actual status. For instance, the changed ventilatory setting value 504 may be represented in a yellow, italicized font. In the alternative, a changed setting value may be represented in any suitable form such that the clinician may be alerted to the fact that the setting has a pending status. For instance, the changed setting value may be displayed with an asterisk, or other indication. Further, note that actual ventilatory setting 508 may continue to display an actual frequency setting value, i.e., 10 breaths/min, until the pending value for changed ventilatory setting value 504 has been accepted by the clinician.

A cancel element 512 may also be provided in the setup animation window 502. Cancel element 512 may enable the clinician to cancel a pending setting value prior to accepting the pending setting value. In that case, the pending setting value may be automatically replaced, again, by an actual setting value and the clinician may either re-enter changes to the actual ventilatory settings or close setup animation window 502. In the alternative, cancel element 512 may both cancel a pending setting value and close setup animation window 502.

In another embodiment, the clinician may accept a pending setting value by selecting accept change element 514. Upon accepting the pending setting value, the pending setting value may become a changed actual setting value and may automatically populate a corresponding actual ventilatory setting 508. Additionally or alternatively, upon accepting the pending setting value, setup animation window 502 may appear to fade away and the settings values of settings access elements 506 may appear to float or fade down and populate the actual ventilatory settings 510. That is, all actual or pending settings values displayed in settings access elements 506, whether settings changes were made or not, may appear to visually populate actual ventilatory settings 510. Thus, a visual indication of the settings changes as they are applied to actual ventilatory settings on the GUI is provided for the clinician.

Figure 6:
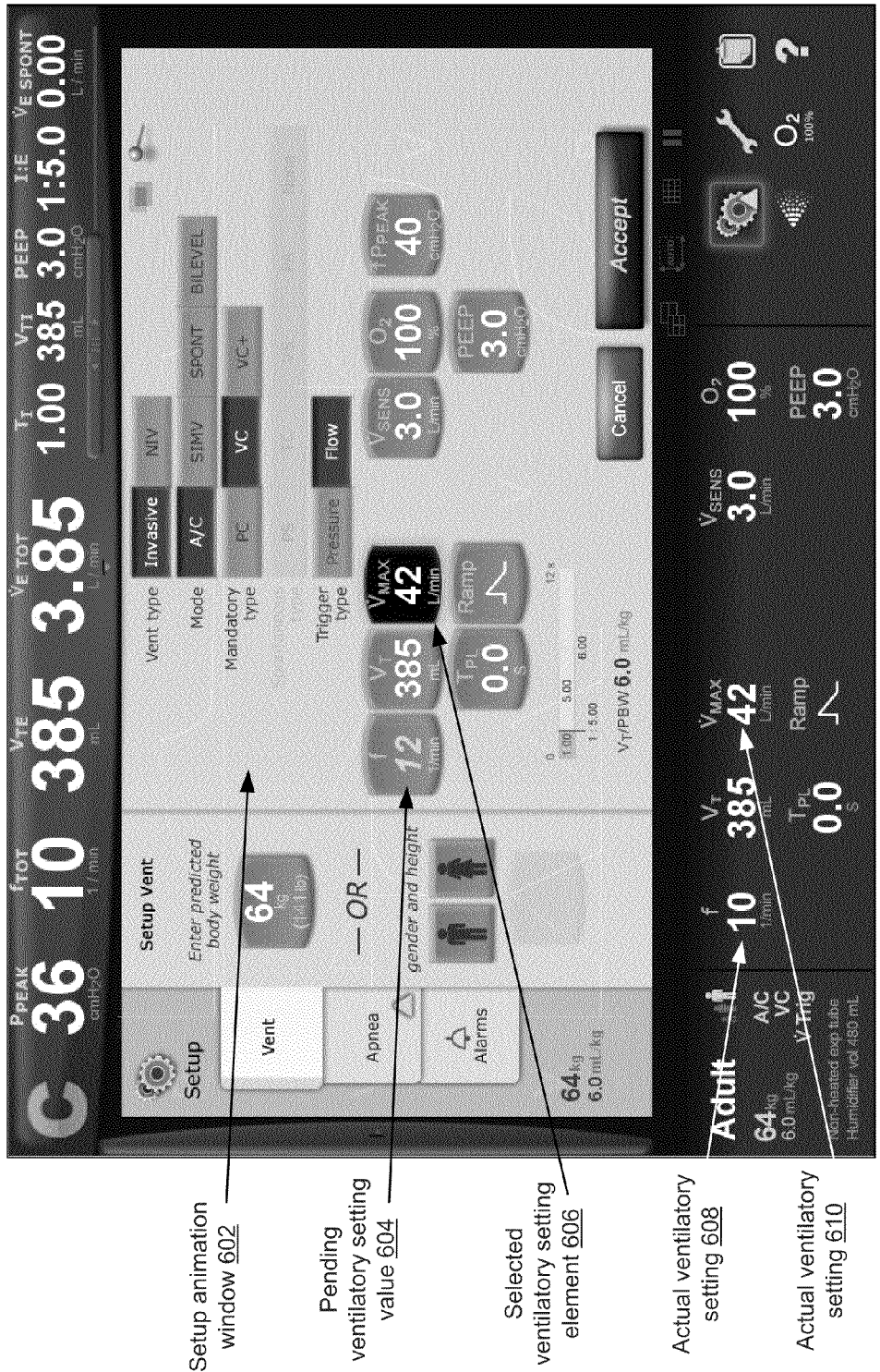
FIG. 6 is an illustration of an embodiment of a graphical user interface displaying a pending status of the change to the setting value of the selected ventilatory setting element.

FIG. 6 is an illustration of an embodiment of a graphical user interface displaying a pending status of the change to the setting value of the selected ventilatory setting element.

For example, FIG. 6 illustrates a pending frequency setting change in a yellow, italicized font, i.e., pending ventilatory setting value 604. In this embodiment, a setting element associated with pending ventilatory setting value 604 is not shown as highlighted or selected within setup animation window 602.

According to the embodiment illustrated in FIG. 6, another ventilatory setting element has been selected, i.e., selected ventilatory setting element 606. As described above, selected ventilatory setting element 606 continues to display an actual ventilatory setting value for maximum flow unless and until the maximum flow setting is changed. As such, the maximum flow value represented in selected ventilatory setting element 606, i.e., 42 L/min, is the same as the maximum flow setting value displayed by actual ventilatory setting 610. In contrast, pending ventilatory setting value 604 is 12 breaths/min, rather than the actual setting value of 10 breaths/min represented in actual ventilatory settings 608.

Figure 7:
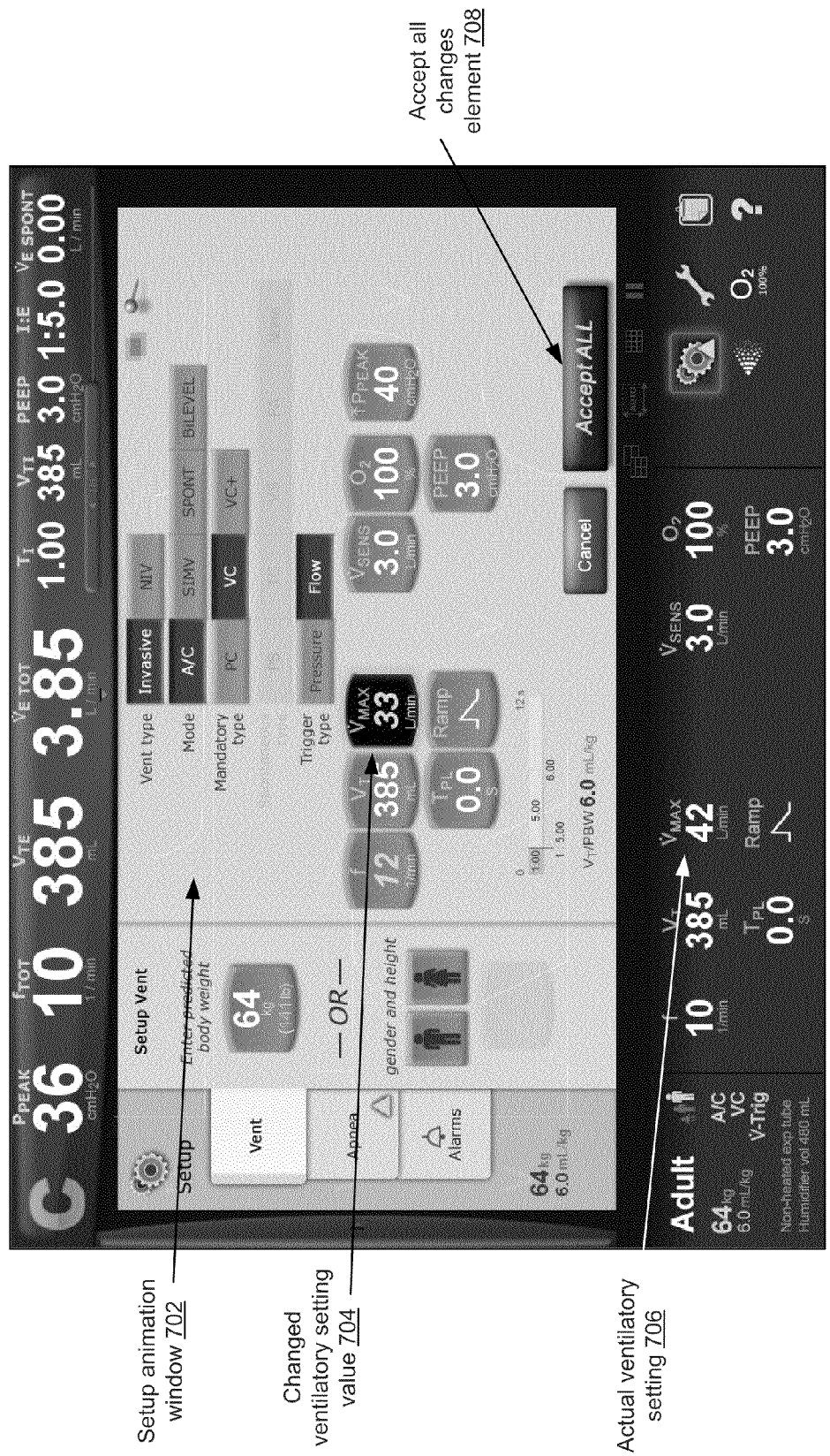
FIG. 7 is an illustration of an embodiment of a graphical user interface displaying an indicator of a plurality of pending ventilatory settings changes on the setup animation window.

FIG. 7 is an illustration of an embodiment of a graphical user interface displaying an indicator of a plurality of pending ventilator), settings changes on the setup animation window.

For example, FIG. 7 illustrates a setting change to an additional ventilatory setting, i.e., changed ventilatory setting value 704. As described above, the changed setting value for maximum flow, i.e., 33 L/min, may be displayed as a pending setting value in yellow italics. Again, as described above, changed ventilatory setting value 704 is different from the actual setting value represented in actual ventilatory setting 706 unless and until pending settings changes are accepted by the clinician.

As illustrated in FIG. 7, when more than one setting change is pending, an accept all changes element 708 may be provided, rather than merely an accept changes element (as described with reference to accept change element 514). Upon accepting all pending settings values, setup animation window 702 may automatically close and actual ventilatory settings may be automatically populated with the accepted pending settings values. Additionally or alternatively, upon accepting the pending settings values, all actual or pending settings values displayed in the settings access elements, whether settings changes were made or not, may appear to visually populate the actual ventilatory settings. Thus, a visual indication of the settings changes as they are applied to actual ventilatory settings on the GUI is provided for the clinician.

Figure 8:
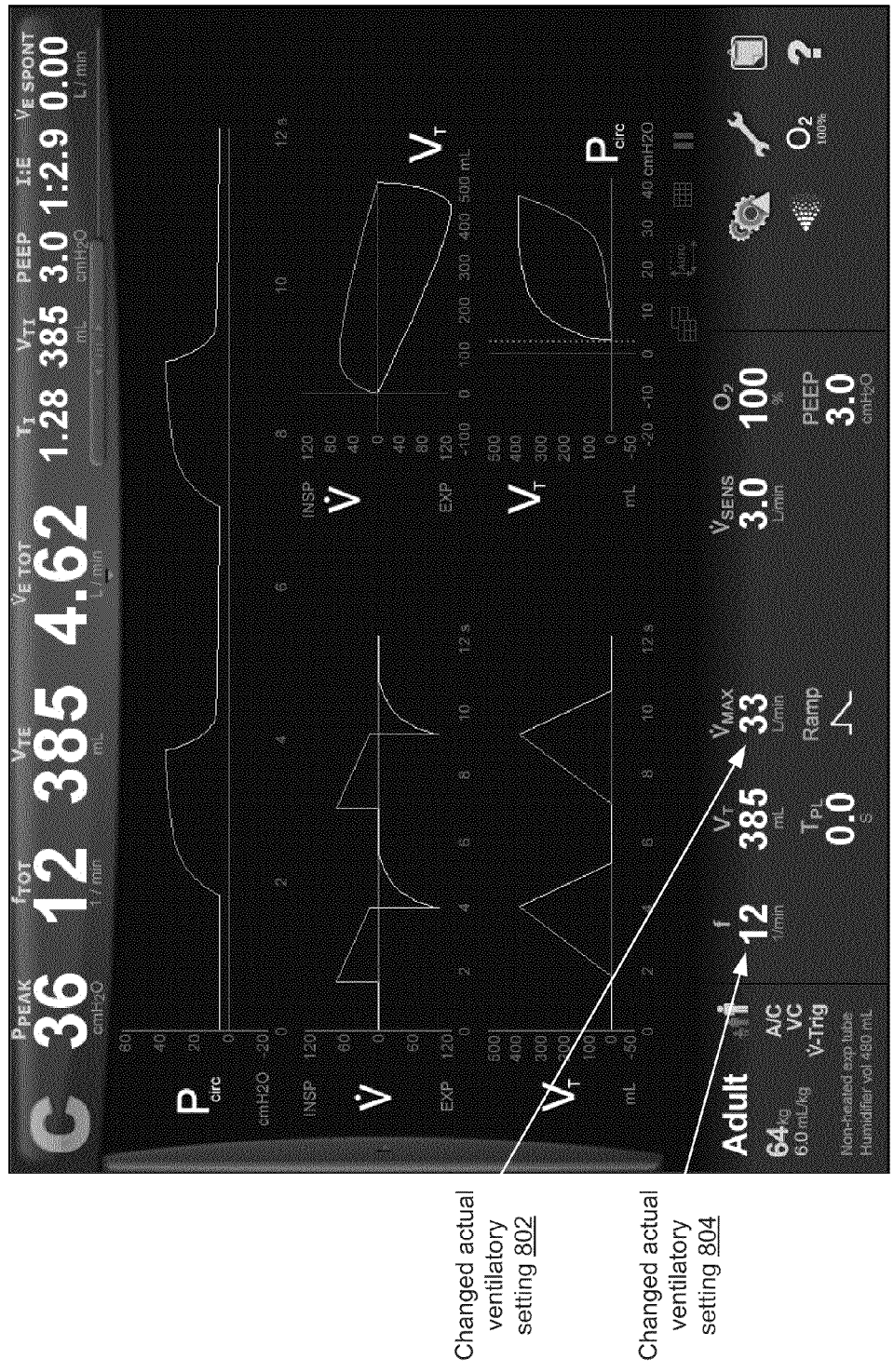
FIG. 8 is an illustration of an embodiment of a graphical user interface displaying changed actual ventilatory settings.

FIG. 8 is an illustration of an embodiment of a graphical user interface displaying changed actual ventilatory settings.

For example, FIG. 8 illustrates a GUI displaying graphical respiratory data and actual ventilatory settings, as initially described with reference to FIG. 2. However, in this case, the actual ventilatory settings have been changed vis-á-vis FIG. 2. That is, by accessing an animation window for adjusting ventilatory settings, changes have been accepted and implemented by the ventilator, as illustrated in FIG. 8. For example, while FIG. 2 shows an actual ventilatory setting 204 with a frequency setting value of 10 breaths/min, FIG. 8 illustrates a changed actual ventilatory setting 802 with a frequency setting value of 12 breaths/min. In addition, while FIG. 2 shows an actual ventilatory setting 204 with a maximum flow value of 42 L/min, FIG. 8 illustrates a changed actual ventilatory setting 804 with a maximum flow value of 33 L/min. As described above, changed actual ventilatory settings 802 and 804 may be represented in a white font to convey to the clinician that the changed ventilatory settings have an actual status and that the changed ventilatory settings are being currently implemented by the ventilator.

Figure 9:
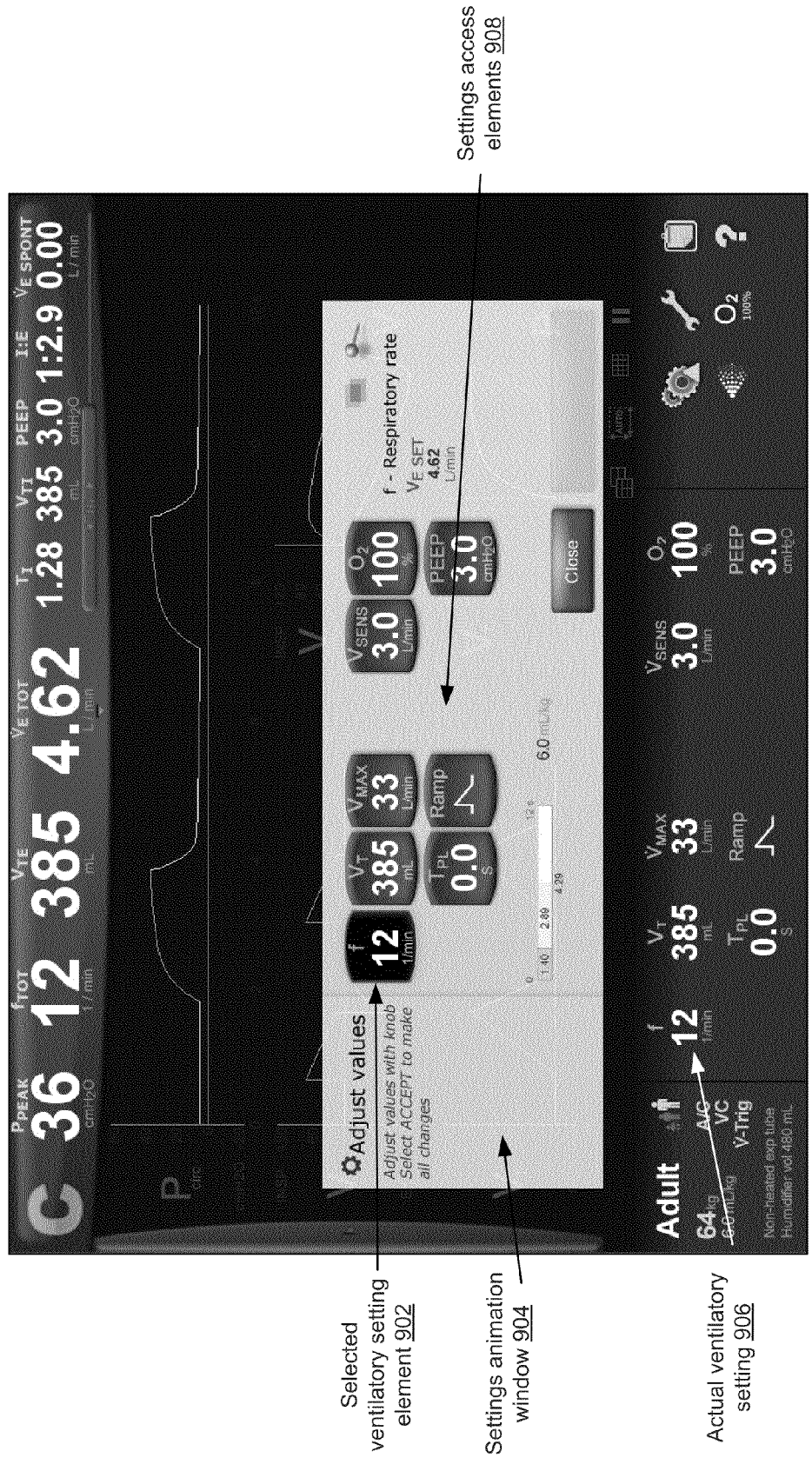
FIG. 9 is an illustration of another embodiment of a graphical user interface displaying a settings animation window for accessing and changing respiratory settings.

FIG. 9 is an illustration of another embodiment of a graphical user interface displaying a settings animation window for accessing and changing respiratory settings.

For example, with reference to changed actual ventilatory settings 802 and 804 as illustrated in FIG. 8, a clinician may desire to undo or otherwise further adjust actual ventilator settings by accessing a settings animation window. As illustrated in FIG. 9, settings animation window 904 may be an abbreviated animation window. That is, rather than displaying multiple setup screens within the animation window, as described above with reference to FIG. 3, the abbreviated animation window may only include access to minimal ventilatory settings. For instance, ventilatory settings for frequency, tidal volume, maximum and minimum flow, etc., as described above, but neglecting additional ventilatory mode and type settings, apnea settings, and alarm settings.

Settings animation window 904 may be accessed by touching, clicking, or otherwise selecting one of a plurality of actual ventilatory settings 906. Settings animation window 904 may be displayed as a single page, boxed window, or other suitable display. Further, when settings animation window 904 is accessed, it may appear to expand from the plurality of actual ventilatory settings 906. In this case, the expanding settings animation window 904 may provide a visual indication that correlates the plurality of actual ventilatory settings 906 with a plurality of settings access elements for adjusting the actual ventilatory settings 906. Alternatively, settings animation window 904 may be displayed as a pop-up window or it may expand from a border of the GUI, for instance.

As illustrated, settings animation window 904 may include settings access elements 908. As described above, settings access elements 908 may be displayed as buttons, tabs, icons, or any other suitable visual access element. Further, the settings access elements 908 may be configured in the same visual arrangement as the plurality of actual ventilatory settings 906, such that a clinician may easily correlate the actual ventilatory settings 906 with the settings access elements 908 used to change them. Upon display of settings animation window 904, a clinician may touch, click, or otherwise select one or more of the settings access elements 908 in order to input or change the ventilatory settings.

As described above, upon accepting the one or more pending settings changes, settings animation window 904 may automatically close and actual ventilatory settings may be automatically populated with the accepted pending settings values. Additionally or alternatively, upon accepting the pending setting value, settings animation window 904 may appear to fade away and the settings values of settings access elements 908 may appear to float or fade down and populate the actual ventilatory settings. Thus, a visual indication of the settings changes as they are applied to actual ventilatory settings on the GUI is provided for the clinician.

Further, as described above, a pin-up feature for the settings animation window 904 may be provided. As such, upon selecting a pin-up icon or other selection element, the settings animation window 904 may be displayed until the clinician desires to "un-pin" or close the settings animation window 904. In this case, the settings animation window 904 may not "time out," but may continue to be displayed to the clinician.

Additionally, a transparency feature may also be provided for the settings animation window. For example, by touching, clicking or otherwise selecting a transparency element, for instance a transparency icon or other selection element, a clinician may adjust the transparency and/or opacity of the settings animation window 904. As such, the clinician may adjust the settings animation window 904 to be highly transparent such that graphical respiratory data may be simultaneously viewed with the settings animation window 904. In the alternative, a clinician may adjust the settings animation window 904 to be highly opaque such that graphical respiratory data may not detract from viewing the settings animation window 904. Alternatively still, the settings animation window 904 may be adjusted to balance transparency and opacity such that both relevant respiratory data and the settings animation window 904 may be easily and simultaneously viewed.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A ventilator comprising a display device, the ventilator configured with a computer having a processor and a memory, the memory communicatively coupled to the processor and containing instructions that, when executed by the processor, cause the ventilator to provide a graphical user interface on the display device, the graphical user interface comprising:
 a first window, the first window comprising:
  a plurality of actual ventilatory settings; and
  a setup icon; and
 a second window, wherein the second window visually expands out from the setup icon upon selection of the setup icon, wherein the second window comprises:
  a plurality of settings access elements corresponding to the plurality of actual ventilatory settings, wherein each setting access element is selectable for adjusting a setting value associated with a corresponding actual ventilatory setting, wherein the adjusting comprises:
   receiving a selection of a setting access element;
   receiving input of an adjusted setting value into the selected setting access element;
   receiving an accept command for the adjusted setting value; and
   in response to the accept command, automatically populating a corresponding actual ventilatory setting by visually floating the adjusted setting value from the selected setting access element in the second window to the corresponding actual ventilatory setting in the first window.

2. The ventilator of claim 1, the second window further comprising:
 a transparency icon; and
 a pin-up icon.

3. The ventilator of claim 2, wherein the plurality of settings access elements are arranged in a same configuration as the plurality of actual ventilatory settings.

4. The ventilator of claim 2, further comprising:
 receiving a selection of the transparency icon; and
 adjusting a transparency of the second window such that graphical data displayed within the first window is simultaneously viewable with the second window.

5. The ventilator of claim 2, further comprising:
 receiving a selection of the pin-up icon; and
 displaying the second window after an accept command until a close command is received.

6. The ventilator of claim 1, further comprising:
 upon receiving a selection of the setting access element of the plurality of settings access elements, associating a visual indication with the selected setting access element.

7. The ventilator of claim 6, wherein an actual setting value is initially associated with the selected setting access element, and wherein upon receiving the input the actual setting value is changed to the adjusted setting value.

8. A ventilatory system for displaying a settings animation window including access elements for changing ventilatory settings, comprising:
   at least one display device;
   at least one processor; and
   at least one memory, communicatively coupled to the at least one processor and containing instructions that, when executed by the at least one processor, provide a graphical user interface on the at least one display, comprising:
      a first window associated with the graphical user interface, the first window comprising:
         a plurality of actual ventilatory settings; and
         a setup icon; and
      a second window, wherein the second window is the settings animation window, wherein the second window visually expands out from the setup icon upon selection of the setup icon, the second window comprising:
         a plurality of settings access elements corresponding to the plurality of actual ventilatory settings, wherein each setting access element is selectable for adjusting a setting value associated with a corresponding actual ventilatory setting, wherein the adjusting comprises:
            receiving a selection of a setting access element;
            receiving input of an adjusted setting value into the selected setting access element;
            receiving an accept command for the adjusted setting value; and
            in response to the accept command, automatically populating a corresponding actual ventilatory setting by visually floating the adjusted setting value from the selected setting access element in the second window to the corresponding actual ventilatory setting in the first window.

9. The ventilatory system of claim 8, the second window further comprising:
   a transparency element.

10. The ventilatory system of claim 9, wherein selection of the transparency element allows graphical data displayed in the at least one window to be simultaneously viewed with the second window.

11. The ventilatory system of claim 9, further comprising:
   upon receiving the input, changing an actual setting value that is initially associated with the selected setting access element to the adjusted setting value.

12. A non-transitory computer-readable storage medium having instructions that when executed provide a graphical user interface for displaying a settings animation window including access elements for changing ventilatory settings, the graphical user interface comprising:
   a first window, the first window comprising:
      a plurality of actual ventilatory settings, wherein selection of at least one of the plurality of actual ventilatory settings initiates display of the settings animation window; and
   a second window, wherein the second window is the settings animation window, wherein the second window visually expands out from the at least one selected actual ventilatory setting, the second window comprising:
      a plurality of settings access elements corresponding to the plurality of actual ventilatory settings, wherein each setting access element is selectable for adjusting a setting value associated with a corresponding actual ventilatory setting, wherein the adjusting comprises:
         receiving a selection of a setting access element;
         receiving input of an adjusted setting value into the selected setting access element;
         receiving an accept command for the adjusted setting value; and
         in response to the accept command, automatically populating a corresponding actual ventilatory setting by visually floating the adjusted setting value from the selected setting access element in the second window to the corresponding actual ventilatory setting in the first window.

13. The non-transitory computer-readable storage medium of claim 12, wherein the non-transitory computer-readable storage medium is selected from a group consisting of: RAM, ROM, EPROM, EEPROM, flash memory, CD-ROM, DVD, magnetic cassettes, magnetic tape, and magnetic disk storage.

* * * * *